(12) United States Patent
Zimmermann et al.

(10) Patent No.: US 10,329,532 B2
(45) Date of Patent: Jun. 25, 2019

(54) METHOD TO DIRECT DIFFERENTIATION OF PLURIPOTENT STEM CELLS INTO FUNCTIONAL HEART MUSCLE

(71) Applicant: GEORG-AUGUST-UNIVERSITÄT GÖTTINGEN STIFTUNG ÖFFENTLICHEN RECHTS, UNIVERSITÄTSMEDIZIN, Göttingen (DE)

(72) Inventors: Wolfram-Hubertus Zimmermann, Göttingen (DE); James Hudson, Queensland Carina Heights (AU); Malte Tiburcy, Göttingen (DE)

(73) Assignee: GEORG-AUGUST-UNIVERSITÄT GÖTTINGEN STIFTUNG ÖFFENTLICHEN RECHTS, UNIVERSITÄTSMEDIZIN, Göttingen (DE)

( * ) Notice: Subject to any disclaimer, the term of this patent is extended or adjusted under 35 U.S.C. 154(b) by 0 days.

(21) Appl. No.: 14/917,103

(22) PCT Filed: Sep. 19, 2014

(86) PCT No.: PCT/EP2014/069951
§ 371 (c)(1),
(2) Date: Mar. 7, 2016

(87) PCT Pub. No.: WO2015/040142
PCT Pub. Date: Mar. 26, 2015

(65) Prior Publication Data
US 2016/0215264 A1    Jul. 28, 2016

(30) Foreign Application Priority Data

Sep. 20, 2013 (EP) .................................. 13185344

(51) Int. Cl.
| | |
|---|---|
| C12N 5/071 | (2010.01) |
| C12N 5/00 | (2006.01) |
| C12N 5/02 | (2006.01) |
| C12N 5/077 | (2010.01) |

(52) U.S. Cl.
CPC ........ *C12N 5/0657* (2013.01); *C12N 2500/25* (2013.01); *C12N 2500/90* (2013.01); *C12N 2501/115* (2013.01); *C12N 2501/155* (2013.01); *C12N 2501/16* (2013.01); *C12N 2501/39* (2013.01); *C12N 2501/415* (2013.01); *C12N 2501/727* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 2004/0014209 A1 | 1/2004 | Lassar et al. | |
| 2009/0061410 A1* | 3/2009 | Zimmermann | ........ C12M 21/08 435/1.1 |
| 2013/0177535 A1 | 7/2013 | Cashman et al. | |
| 2013/0189785 A1* | 7/2013 | Palecek | ................ C12N 5/0657 435/377 |
| 2015/0017718 A1 | 1/2015 | Nakatsuji et al. | |

FOREIGN PATENT DOCUMENTS

| | | |
|---|---|---|
| JP | 2011-512855 A | 4/2011 |
| WO | WO 2009/007852 A2 | 1/2009 |
| WO | WO 2009/036982 A1 | 3/2009 |
| WO | WO 2010/011352 A2 | 1/2010 |
| WO | WO 2010/144678 A2 | 12/2010 |
| WO | WO 2013/013206 A1 | 1/2013 |
| WO | WO 2013/056072 A1 | 4/2013 |
| WO | WO 2013/063305 A2 | 5/2013 |
| WO | WO 2013/111875 A1 | 8/2013 |

OTHER PUBLICATIONS

Uosaki et al., PLoS ONE, 6(8)e23657:1-9 (2011).*
Yang et al., Nature Let., 453:524-529 (2008).*
Goumans et al., Stem Cell Res., 1:138-149 (2008).*
Long et al., Biochem. Biophys. Res. Comm., 388:700-704 (2009).*
Pakzad et al., Stem Cell Rev. Rep., 6:96-107 (2010).*
Burridge et al., Cell Stem Cell, 10(1):16-28 (2012).*
Decker et al., He art Circ. Physiol., 41: H2902-H2918 (1997).*
Geuss et al., Biotechnol. Prog., 29:1089-1096 (2013).*
Heng et al., Cardiovas. Res., 62:34-42 (2004).*
Mummery et al., Circ Res., 111(3): 344-358 (2012).*
Shimko et al., Tiss. Eng. A, 14(1):49-58 (2008).*
Watanabe et al., Nature Biotechnol., 25(6):681-686 (2007).*
Vandenburgh et al., Am. J. Physiol. 270:C1284-C1292 (1996).*
Bird et al. "The human adult cardiomyocyte phenotype", Cardiovascular Research, 58, (2003), pp. 423-434.
Brown et al. "Analysis of Oxygen Transport in a Diffusion-Limited Model of Engineered Heart Tissue", Biotechnology and Bioengineering, vol. 97, No. 4, pp. 962-975, Jul. 1, 2007.
Campos et al. "Chromosomal Spread Preparation of Human Embryonic Stem Cells for Karyotyping", Journal of Visualized Experiments 4, (2009).

(Continued)

*Primary Examiner* — Thomas J. Visone
(74) *Attorney, Agent, or Firm* — Birch, Stewart, Kolasch & Birch, LLP

(57) ABSTRACT

The present invention is directed to a method for producing bioengineered heart muscle (BHM) from pluripotent stem cells, generally comprising the steps of inducing mesoderm differentiation, cardiac differentiation, and cardiac maturation by directed tissue formation. The method is a robust, serum-free and reproducible way to produce BHM for multiple applications, and is applicable to multiple pluripotent stem cell lines. The present invention is also directed to the BHM produced by the method disclosed herein, as well as to uses of said BHM in pharmacologic and toxicity screenings, and its use in medicine.

23 Claims, 16 Drawing Sheets

Specification includes a Sequence Listing.

(56) References Cited

OTHER PUBLICATIONS

Cao et al. "Ascorbic acid enhances the cardiac differentiation of induced pluripotent stem cells through promoting the proliferation of cardiac progenitor cells", Cell Research, (2012), 22:219-236.

Carvajal-Vergara et al. "Patient-specific induced pluripotent stem cell derived models of Leopard syndrome", Nature, Jun. 10, 2010, 465(7299): 808-812.

Chan et al. "Live cell imaging distinguishes bona fide human iPS cells from partially reprogrammed cells", Nature Biotechnology, vol. 27, pp. 1033-1037, Nov. 2009.

Didié et al. "Parthenogenetic stem cells for tissue-engineered heart repair", The Journal of Clinical Investigation 123, pp. 1285-1298, (2013).

Dierickx et al. "Embryonic Template-Based Generation and Purification of Pluripotent Stem Cell-Derived Cardiomyocytes for Heart Repair", J. of Cardiovasc. Trans. Res., (2012), vol. 5, No. 5, pp. 566-580.

Ellerström et al. "Facilitated Expansion of Human Embryonic Stem Cells by Single-Cell Enzymatic Dissociation", Stem Cells 25, pp. 1690-1696, (2007).

Eschenhagen et al. "Physiological aspects of cardiac tissue engineering", Am J Physiol Heart Circ Physiol 303, H133-H143, 2012.

Eschenhagen et al. "Three-dimensional reconstitution of embryonic cardiomyocytes in a collagen matrix: a new heart muscle model system", FASEB J., 11, pp. 683-694, (1997).

Freberg et al. "Epigenetic Reprogramming of OCT4 and NANOG Regulatory Regions by Embryonal Carcinoma Cell Extract", Molecular Biology of the Cell, vol. 18, pp. 1543-1553, May 2007.

Hudson et al. "Development of Myocardial Constructs Using Modulus-Matched Acrylated Polypropylene Glycol Triol Substrate and Different Nonmyocyte Cell Populations", Tissue Engineering: Part A, vol. 17, Nos. 17 and 18, 2011.

Hudson et al. "Primitive Cardiac Cells from Human Embryonic Stem Cells", Stem Cells and Development, vol. 21, No. 9, 2012, pp. 1513-1523.

Hudson et al. "Tuning Wnt-signaling to enhance cardiomyogenesis in human embryonic and induced pluripotent stem cells", Journal of Molecular and Cellular Cardiology, vol. 51, No. 3, 2011, pp. 277-279.

International Search Report, issued in PCT/EP2014/069951, PCT/ISA/210, dated Dec. 18, 2014.

Irion et al. "Identification and targeting of the ROSA26 locus in human embryonic stem cells", Nature Biotechnology, vol. 25, No. 12, pp. 1477-1482, Dec. 2007.

Itzhaki et al. "Modelling the long QT syndrome with induced pluripotent stem cells", Nature, vol. 471, pp. 225-229, Mar. 10, 2011.

Kattman et al. "Stage-Specific Optimization of Activin/Nodal and BMP Signaling Promotes Cardiac Differentiation of Mouse and Human Pluripotent Stem Cell Lines", Cell Stem Cell 8, pp. 228-240, Feb. 4, 2011.

Kehat et al. "Human embryonic stem cells can differentiate into myocytes with structural and functional properties of cardiomyocytes", The Journal of Clinical Investigation, vol. 108, No. 3, Aug. 2001.

Kruithof et al. "TGFβ and BMP signaling in cardiac cushion formation: Lessons from mice and chicken", Differentiation, 84, (2012), pp. 89-102.

Lian et al. "Directed cardiomyocyte differentiation from human pluripotent stem cells by modulating Wnt/β-catenin signaling under fully defined conditions", Nature Protocols, vol. 8, No. 1, pp. 162-174, (2013).

Lian et al. "Insulin inhibits cardiac mesoderm, not mesendoderm, formation during cardiac differentiation of human pluripotent stem cells and modulation of canonical Wnt signaling can rescue this inhibition", Stem Cells, Mar. 2013, 31(3), pp. 447-457.

Malan et al. "Cardiomyocytes Obtained From Induced Pluripotent Stem Cells With Long-QT Syndrome 3 Recapitulate Typical Disease-Specific Features In Vitro", Circulation Research 109(8), pp. 841-847, (2011).

Mauritz et al. "Generation of Functional Murine Cardiac Myocytes From Induced Pluripotent Stem Cells", Circulation, vol. 118, No. 5, pp. 507-517, (2008).

Moretti et al. "Patient-Specific Induced Pluripotent Stem-Cell Models for Long-QT Syndrome", The New England Journal of Medicine, vol. 363, No. 15, Oct. 7, 2010, pp. 1397-1409.

Naito et al. "Optimizing Engineered Heart Tissue for Therapeutic Applications as Surrogate Heart Muscle", Circulation 2006, 114, I-72-I-78.

Neagoe et al. "Titin Isoform Switch in Ischemic Human Heart Disease", Circulation 106, pp. 1333-1341, (2002).

Park et al. "Reprogramming of human somatic cells to pluripotency with defined factors", Nature, vol. 451, pp. 141-146, Jan. 10, 2008.

Schaaf et al. "Human Engineered Heart Tissue as a Versatile Tool in Basic Research and Preclinical Toxicology", PLoS ONE, Oct. 2011, vol. 6, Issue 10, e26397.

Soong et al. "Cardiac Differentiation of Human Embryonic Stem Cells and their Assembly into Engineered Heart Muscle", Current Protocols in Cell Biology, vol. 55, Unit 23.8.1-23.8.21, Jun. 2012.

Soong et al. "Development of a novel technology to engineer heart muscle for contractile and paracrine support in heart failure", Internet Citation, 2012.

Takahashi et al. "Induction of Pluripotent Stem Cells from Adult Human Fibroblasts by Defined Factors", Cell 131, pp. 861-872, Nov. 30, 2007.

Takahashi et al. "Induction of Pluripotent Stem Cells from Mouse Embryonic and Adult Fibroblast Cultures by Defined Factors", Cell 126, pp. 663-676, Aug. 25, 2006.

Thomson et al. "Embryonic Stem Cell Lines Derived from Human Blastocysts", Science, vol. 282, Nov. 6, 1998, pp. 1145-1147.

Tiburcy et al. "Terminal Differentiation, Advanced Organotypic Maturation, and Modeling of Hypertrophic Growth in Engineered Heart Tissue", Circulation Research 109, pp. 1105-1114, (2011).

Tulloch et al. "Growth of Engineered Human Myocardium with Mechanical Loading and Vascular Co-culture", Circulation Research 109, pp. 47-59, (2011).

Written Opinion of the International Searching Authority, issued in PCT/EP2014/069951, PCT/ISA/237, dated Dec. 18, 2014.

Yazawa et al. "Using IPS cells to investigate cardiac phenotypes in patients with Timothy Syndrome", Nature 471, pp. 230-234, Mar. 10, 2011.

Zhang et al. "Functional Cardiomyocytes Derived from Human Induced Pluripotent Stem Cells", Circulation Research 104, e30-41, Feb. 27, 2009.

Zimmermann et al. "Engineered heart tissue grafts improve systolic and diastolic function in infarcted rat hearts", Nature Medicine, vol. 12, No. 4, Apr. 2006, pp. 452-458.

Zimmermann et al. "Three-Dimensional Engineered Heart Tissue from Neonatal Rat Cardiac Myocytes", Biotechnology and Bioengineering, vol. 68, No. 1, Apr. 5, 2000, pp. 106-114.

Zimmermann et al. "Tissue Engineering of a Differentiated Cardiac Muscle Construct", Circulation Research 90, pp. 223-230, (2002).

Development of a method for inducing cardiomyocytes apt for clinical application from human ES/iPS cells, A great contribution to the achievement of a safe/feasible/highly efficient regenerative medicine, News release at the website of iCeMS of Kyoto University, Oct. 26, 2012, www.kyoto-u.ac.jp/static/ja/news_data/h/h1/news6/2012/121026_1.h.

Japanese Office Action issued in corresponding Japanese Patent Application No. 2016-515530 dated May 22, 2018.

Zimmermann, W.H., et al. "Heart muscle engineering: An update on cardiac muscle replacement therapy" Cardiovascular Research, 71 (2006) pp. 419-429.

* cited by examiner

SEQUENCE LISTING

```
<160> NUMBER OF SEQ ID NOS: 80

<210> SEQ ID NO 1
<211> LENGTH: 22
<212> TYPE: DNA
<213> ORGANISM: Artificial
<220> FEATURE:
<223> OTHER INFORMATION: Primer GAPDH F

<400> SEQUENCE: 1
cctcaagatc atcagcaatg cc                                              22

<210> SEQ ID NO 2
<211> LENGTH: 19
<212> TYPE: DNA
<213> ORGANISM: Artificial
<220> FEATURE:
<223> OTHER INFORMATION: Primer GAPDH R
```

```
<400> SEQUENCE: 2
atgttctgga gagccccgc                                                19

<210> SEQ ID NO 3
<211> LENGTH: 19
<212> TYPE: DNA
<213> ORGANISM: Artificial
<220> FEATURE:
<223> OTHER INFORMATION: Primer OCT4 F

<400> SEQUENCE: 3
cagtgcccga aacccacac                                                19

<210> SEQ ID NO 4
<211> LENGTH: 20
<212> TYPE: DNA
<213> ORGANISM: Artificial
<220> FEATURE:
<223> OTHER INFORMATION: Primer OCT4 R

<400> SEQUENCE: 4
ggagacccag cagcctcaaa                                               20

<210> SEQ ID NO 5
<211> LENGTH: 20
<212> TYPE: DNA
<213> ORGANISM: Artificial
<220> FEATURE:
<223> OTHER INFORMATION: Primer NANOG F

<400> SEQUENCE: 5
cagaaggcct cagcacctac                                               20

<210> SEQ ID NO 6
<211> LENGTH: 20
<212> TYPE: DNA
<213> ORGANISM: Artificial
<220> FEATURE:
<223> OTHER INFORMATION: Primer NANOG R

<400> SEQUENCE: 6
attgttccag gtctggttgc                                               20

<210> SEQ ID NO 7
<211> LENGTH: 23
<212> TYPE: DNA
<213> ORGANISM: Artificial
<220> FEATURE:
<223> OTHER INFORMATION: Primer REX1 F

<400> SEQUENCE: 7
caccgcctcc cttgggaatt cag                                           23

<210> SEQ ID NO 8
<211> LENGTH: 24
<212> TYPE: DNA
<213> ORGANISM: Artificial
<220> FEATURE:
<223> OTHER INFORMATION: Primer REX1 R

<400> SEQUENCE: 8
tgttctgttc acacaggctc cagc                                          24

<210> SEQ ID NO 9
<211> LENGTH: 23
```

-continued

```
<212> TYPE: DNA
<213> ORGANISM: Artificial
<220> FEATURE:
<223> OTHER INFORMATION: Primer DNMT3B F

<400> SEQUENCE: 9
ggcccaagta aacctagctc ggc                                          23

<210> SEQ ID NO 10
<211> LENGTH: 23
<212> TYPE: DNA
<213> ORGANISM: Artificial
<220> FEATURE:
<223> OTHER INFORMATION: Primer DNMT3B R

<400> SEQUENCE: 10
atgcctggtg tctcccttca tgc                                          23

<210> SEQ ID NO 11
<211> LENGTH: 20
<212> TYPE: DNA
<213> ORGANISM: Artificial
<220> FEATURE:
<223> OTHER INFORMATION: Primer MIXL1 F

<400> SEQUENCE: 11
ccgagtccag gatccaggta                                              20

<210> SEQ ID NO 12
<211> LENGTH: 19
<212> TYPE: DNA
<213> ORGANISM: Artificial
<220> FEATURE:
<223> OTHER INFORMATION: Primer MIXL1 R

<400> SEQUENCE: 12
ctctgacgcc gagacttgg                                               19

<210> SEQ ID NO 13
<211> LENGTH: 21
<212> TYPE: DNA
<213> ORGANISM: Artificial
<220> FEATURE:
<223> OTHER INFORMATION: Primer NKX2-5 F

<400> SEQUENCE: 13
acaacttcgt gaacttcggc g                                            21

<210> SEQ ID NO 14
<211> LENGTH: 22
<212> TYPE: DNA
<213> ORGANISM: Artificial
<220> FEATURE:
<223> OTHER INFORMATION: Primer NKX2-5 R

<400> SEQUENCE: 14
gtggacactc ccgagttgct ct                                           22

<210> SEQ ID NO 15
<211> LENGTH: 20
<212> TYPE: DNA
<213> ORGANISM: Artificial
<220> FEATURE:
<223> OTHER INFORMATION: Primer TBX5 F

<400> SEQUENCE: 15
```
tcataaccaa ggctggaagg                                           20

<210> SEQ ID NO 16
<211> LENGTH: 20
<212> TYPE: DNA
<213> ORGANISM: Artificial
<220> FEATURE:
<223> OTHER INFORMATION: Primer TBX5 R

<400> SEQUENCE: 16
gcccgtcaca gaccatttat                                           20

<210> SEQ ID NO 17
<211> LENGTH: 20
<212> TYPE: DNA
<213> ORGANISM: Artificial
<220> FEATURE:
<223> OTHER INFORMATION: Primer ISL1 F

<400> SEQUENCE: 17
cgccttgcag agtgacatag                                           20

<210> SEQ ID NO 18
<211> LENGTH: 20
<212> TYPE: DNA
<213> ORGANISM: Artificial
<220> FEATURE:
<223> OTHER INFORMATION: Primer ISL1 R

<400> SEQUENCE: 18
ggactggcta ccatgctgtt                                           20

<210> SEQ ID NO 19
<211> LENGTH: 20
<212> TYPE: DNA
<213> ORGANISM: Artificial
<220> FEATURE:
<223> OTHER INFORMATION: Primer MYH6 F

<400> SEQUENCE: 19
ctcctcctac gcaactgccg                                           20

<210> SEQ ID NO 20
<211> LENGTH: 21
<212> TYPE: DNA
<213> ORGANISM: Artificial
<220> FEATURE:
<223> OTHER INFORMATION: Primer MYH6 R

<400> SEQUENCE: 20
cgacaccgtc tggaaggatg a                                         21

<210> SEQ ID NO 21
<211> LENGTH: 20
<212> TYPE: DNA
<213> ORGANISM: Artificial
<220> FEATURE:
<223> OTHER INFORMATION: Primer MYH7 F

<400> SEQUENCE: 21
gaccagatga atgagcaccg                                           20

<210> SEQ ID NO 22
<211> LENGTH: 21
<212> TYPE: DNA
<213> ORGANISM: Artificial

```
<220> FEATURE:
<223> OTHER INFORMATION: Primer MYH7 R

<400> SEQUENCE: 22
ggtgaggtcg ttgacagaac g                                              21

<210> SEQ ID NO 23
<211> LENGTH: 20
<212> TYPE: DNA
<213> ORGANISM: Artificial
<220> FEATURE:
<223> OTHER INFORMATION: Primer MLC2v F

<400> SEQUENCE: 23
ggcgccaact ccaacgtgtt                                                20

<210> SEQ ID NO 24
<211> LENGTH: 20
<212> TYPE: DNA
<213> ORGANISM: Artificial
<220> FEATURE:
<223> OTHER INFORMATION: Primer MLC2v R

<400> SEQUENCE: 24
acgttcactc gcccaagggc                                                20

<210> SEQ ID NO 25
<211> LENGTH: 21
<212> TYPE: DNA
<213> ORGANISM: Artificial
<220> FEATURE:
<223> OTHER INFORMATION: Primer ACTA1 F

<400> SEQUENCE: 25
acccagatca tgtttgagac c                                              21

<210> SEQ ID NO 26
<211> LENGTH: 20
<212> TYPE: DNA
<213> ORGANISM: Artificial
<220> FEATURE:
<223> OTHER INFORMATION: Primer ACTA1 R

<400> SEQUENCE: 26
tcataaatgg gcacgttgtg                                                20

<210> SEQ ID NO 27
<211> LENGTH: 20
<212> TYPE: DNA
<213> ORGANISM: Artificial
<220> FEATURE:
<223> OTHER INFORMATION: Primer NPPA F

<400> SEQUENCE: 27
tctgccctcc taaaaagcaa                                                20

<210> SEQ ID NO 28
<211> LENGTH: 20
<212> TYPE: DNA
<213> ORGANISM: Artificial
<220> FEATURE:
<223> OTHER INFORMATION: Primer NPPA R

<400> SEQUENCE: 28
tgtcctccct ggctgttatc                                                20
```

<210> SEQ ID NO 29
<211> LENGTH: 21
<212> TYPE: DNA
<213> ORGANISM: Artificial
<220> FEATURE:
<223> OTHER INFORMATION: Primer CASQ2 F

<400> SEQUENCE: 29
tcttgcaggg cagaagaggg g                                          21

<210> SEQ ID NO 30
<211> LENGTH: 21
<212> TYPE: DNA
<213> ORGANISM: Artificial
<220> FEATURE:
<223> OTHER INFORMATION: Primer CASQ2 R

<400> SEQUENCE: 30
ggacctgggc cacaagctca a                                          21

<210> SEQ ID NO 31
<211> LENGTH: 20
<212> TYPE: DNA
<213> ORGANISM: Artificial
<220> FEATURE:
<223> OTHER INFORMATION: Primer NEUROD1 F

<400> SEQUENCE: 31
agccacggat caatcttctc                                            20

<210> SEQ ID NO 32
<211> LENGTH: 20
<212> TYPE: DNA
<213> ORGANISM: Artificial
<220> FEATURE:
<223> OTHER INFORMATION: Primer NEUROD1 R

<400> SEQUENCE: 32
gcgtgcctct aatcatgaaa                                            20

<210> SEQ ID NO 33
<211> LENGTH: 20
<212> TYPE: DNA
<213> ORGANISM: Artificial
<220> FEATURE:
<223> OTHER INFORMATION: Primer CDH1 F

<400> SEQUENCE: 33
gaacgcattg ccacatacac                                            20

<210> SEQ ID NO 34
<211> LENGTH: 20
<212> TYPE: DNA
<213> ORGANISM: Artificial
<220> FEATURE:
<223> OTHER INFORMATION: Primer CDH1 R

<400> SEQUENCE: 34
attcgggctt gttgtcattc                                            20

<210> SEQ ID NO 35
<211> LENGTH: 20
<212> TYPE: DNA
<213> ORGANISM: Artificial
<220> FEATURE:
<223> OTHER INFORMATION: Primer CDH2 F

<400> SEQUENCE: 35
cctggaacgc agtgtacaga                                              20

<210> SEQ ID NO 36
<211> LENGTH: 20
<212> TYPE: DNA
<213> ORGANISM: Artificial
<220> FEATURE:
<223> OTHER INFORMATION: CDH2 R

<400> SEQUENCE: 36
tggtttgacc acggtgacta                                              20

<210> SEQ ID NO 37
<211> LENGTH: 20
<212> TYPE: DNA
<213> ORGANISM: Artificial
<220> FEATURE:
<223> OTHER INFORMATION: Primer SNAIL1 F

<400> SEQUENCE: 37
agcgagctgc aggactctaa                                              20

<210> SEQ ID NO 38
<211> LENGTH: 20
<212> TYPE: DNA
<213> ORGANISM: Artificial
<220> FEATURE:
<223> OTHER INFORMATION: Primer SNAIL1 R

<400> SEQUENCE: 38
ggacagagtc ccagatgagc                                              20

<210> SEQ ID NO 39
<211> LENGTH: 23
<212> TYPE: DNA
<213> ORGANISM: Artificial
<220> FEATURE:
<223> OTHER INFORMATION: Primer MESP1 F

<400> SEQUENCE: 39
agcccaagtg acaagggaca act                                          23

<210> SEQ ID NO 40
<211> LENGTH: 24
<212> TYPE: DNA
<213> ORGANISM: Artificial
<220> FEATURE:
<223> OTHER INFORMATION: MESP1 R

<400> SEQUENCE: 40
aaggaaccac ttcgaaggtg ctga                                         24

<210> SEQ ID NO 41
<211> LENGTH: 24
<212> TYPE: DNA
<213> ORGANISM: Artificial
<220> FEATURE:
<223> OTHER INFORMATION: Primer SOX17 F

<400> SEQUENCE: 41
aggaaatcct cagactcctg ggtt                                         24

<210> SEQ ID NO 42

```
<211> LENGTH: 24
<212> TYPE: DNA
<213> ORGANISM: Artificial
<220> FEATURE:
<223> OTHER INFORMATION: Primer SOX17 R

<400> SEQUENCE: 42
cccaaactgt tcaagtggca gaca                                              24

<210> SEQ ID NO 43
<211> LENGTH: 20
<212> TYPE: DNA
<213> ORGANISM: Artificial
<220> FEATURE:
<223> OTHER INFORMATION: Primer ATP2A2 F

<400> SEQUENCE: 43
acctcatctc gtccaacgtc                                                   20

<210> SEQ ID NO 44
<211> LENGTH: 20
<212> TYPE: DNA
<213> ORGANISM: Artificial
<220> FEATURE:
<223> OTHER INFORMATION: Primer ATP2A2 R

<400> SEQUENCE: 44
tgtcaccaga ttgacccaga                                                   20

<210> SEQ ID NO 45
<211> LENGTH: 20
<212> TYPE: DNA
<213> ORGANISM: Artificial
<220> FEATURE:
<223> OTHER INFORMATION: Primer PLN F

<400> SEQUENCE: 45
acagctgcca aggctaccta                                                   20

<210> SEQ ID NO 46
<211> LENGTH: 20
<212> TYPE: DNA
<213> ORGANISM: Artificial
<220> FEATURE:
<223> OTHER INFORMATION: PLN R

<400> SEQUENCE: 46
tccatgatac cagcaggaca                                                   20

<210> SEQ ID NO 47
<211> LENGTH: 20
<212> TYPE: DNA
<213> ORGANISM: Artificial
<220> FEATURE:
<223> OTHER INFORMATION: Primer RYR2 F

<400> SEQUENCE: 47
tgcaagactc accgaagatg                                                   20

<210> SEQ ID NO 48
<211> LENGTH: 20
<212> TYPE: DNA
<213> ORGANISM: Artificial
<220> FEATURE:
<223> OTHER INFORMATION: Primer RYR2 R

<400> SEQUENCE: 48
```

-continued ccacccagac attagcaggt                                         20

<210> SEQ ID NO 49
<211> LENGTH: 20
<212> TYPE: DNA
<213> ORGANISM: Artificial
<220> FEATURE:
<223> OTHER INFORMATION: Primer COL1A1 F

<400> SEQUENCE: 49
gtgctaaagg tgccaatggt                                         20

<210> SEQ ID NO 50
<211> LENGTH: 20
<212> TYPE: DNA
<213> ORGANISM: Artificial
<220> FEATURE:
<223> OTHER INFORMATION: Primer COL1A1 R

<400> SEQUENCE: 50
accaggttca ccgctgttac                                         20

<210> SEQ ID NO 51
<211> LENGTH: 20
<212> TYPE: DNA
<213> ORGANISM: Artificial
<220> FEATURE:
<223> OTHER INFORMATION: Primer COL3A1 F

<400> SEQUENCE: 51
ccaggagcta acggtctcag                                         20

<210> SEQ ID NO 52
<211> LENGTH: 20
<212> TYPE: DNA
<213> ORGANISM: Artificial
<220> FEATURE:
<223> OTHER INFORMATION: Primer COL3A1 R

<400> SEQUENCE: 52
cagggtttcc atctcttcca                                         20

<210> SEQ ID NO 53
<211> LENGTH: 20
<212> TYPE: DNA
<213> ORGANISM: Artificial
<220> FEATURE:
<223> OTHER INFORMATION: Primer COL5A1 F

<400> SEQUENCE: 53
gacacctcca actcctccaa                                         20

<210> SEQ ID NO 54
<211> LENGTH: 20
<212> TYPE: DNA
<213> ORGANISM: Artificial
<220> FEATURE:
<223> OTHER INFORMATION: Primer COL5A1 R

<400> SEQUENCE: 54
agtgaactcc ccctccaagt                                         20

<210> SEQ ID NO 55
<211> LENGTH: 20
<212> TYPE: DNA

```
<213> ORGANISM: Artificial
<220> FEATURE:
<223> OTHER INFORMATION: Primer COL4A1 F

<400> SEQUENCE: 55
gttggtctac cgggactcaa                                          20

<210> SEQ ID NO 56
<211> LENGTH: 20
<212> TYPE: DNA
<213> ORGANISM: Artificial
<220> FEATURE:
<223> OTHER INFORMATION: Primer COL4A1 R

<400> SEQUENCE: 56
gttcacctct gatcccctga                                          20

<210> SEQ ID NO 57
<211> LENGTH: 20
<212> TYPE: DNA
<213> ORGANISM: Artificial
<220> FEATURE:
<223> OTHER INFORMATION: Primer LAMC1 F

<400> SEQUENCE: 57
gtgagaggtg ccgagagaac                                          20

<210> SEQ ID NO 58
<211> LENGTH: 20
<212> TYPE: DNA
<213> ORGANISM: Artificial
<220> FEATURE:
<223> OTHER INFORMATION: Primer LAMC1 R

<400> SEQUENCE: 58
gtgcttagag agcccacagg                                          20

<210> SEQ ID NO 59
<211> LENGTH: 20
<212> TYPE: DNA
<213> ORGANISM: Artificial
<220> FEATURE:
<223> OTHER INFORMATION: Primer TGFB2 F

<400> SEQUENCE: 59
cgaacccaaa gggtacaatg                                          20

<210> SEQ ID NO 60
<211> LENGTH: 20
<212> TYPE: DNA
<213> ORGANISM: Artificial
<220> FEATURE:
<223> OTHER INFORMATION: Primer TGFB2 R

<400> SEQUENCE: 60
taagctcagg accctgctgt                                          20

<210> SEQ ID NO 61
<211> LENGTH: 22
<212> TYPE: DNA
<213> ORGANISM: Artificial
<220> FEATURE:
<223> OTHER INFORMATION: Primer TTN Ex49-50 F

<400> SEQUENCE: 61
gtaaaaagag ctgccccagt ga                                       22
```

<210> SEQ ID NO 62
<211> LENGTH: 21
<212> TYPE: DNA
<213> ORGANISM: Artificial
<220> FEATURE:
<223> OTHER INFORMATION: Primer TTN Ex49-50 R

<400> SEQUENCE: 62
gctaggtggc ccagtgctac t                                              21

<210> SEQ ID NO 63
<211> LENGTH: 19
<212> TYPE: DNA
<213> ORGANISM: Artificial
<220> FEATURE:
<223> OTHER INFORMATION: Primer TTN Ex107-108 F

<400> SEQUENCE: 63
cagcagaact cagaatcga                                                 19

<210> SEQ ID NO 64
<211> LENGTH: 21
<212> TYPE: DNA
<213> ORGANISM: Artificial
<220> FEATURE:
<223> OTHER INFORMATION: Primer TTN Ex107-108 R

<400> SEQUENCE: 64
atcaaaggac acttcacact c                                              21

<210> SEQ ID NO 65
<211> LENGTH: 21
<212> TYPE: DNA
<213> ORGANISM: Artificial
<220> FEATURE:
<223> OTHER INFORMATION: Primer TTN Ex50-219 F

<400> SEQUENCE: 65
ccaatgagta tggcagtgtc a                                              21

<210> SEQ ID NO 66
<211> LENGTH: 21
<212> TYPE: DNA
<213> ORGANISM: Artificial
<220> FEATURE:
<223> OTHER INFORMATION: Primer TTN Ex50-219 R

<400> SEQUENCE: 66
tacgttccgg aagtaatttg c                                              21

<210> SEQ ID NO 67
<211> LENGTH: 20
<212> TYPE: DNA
<213> ORGANISM: Artificial
<220> FEATURE:
<223> OTHER INFORMATION: Primer endoOCT4 F

<400> SEQUENCE: 67
cctcacttca ctgcactgta                                                20

<210> SEQ ID NO 68
<211> LENGTH: 20
<212> TYPE: DNA
<213> ORGANISM: Artificial
<220> FEATURE:

<223> OTHER INFORMATION: Primer endoOCT4 R

<400> SEQUENCE: 68 caggtttct ttccctagct                                                  20

<210> SEQ ID NO 69
<211> LENGTH: 19
<212> TYPE: DNA
<213> ORGANISM: Artificial
<220> FEATURE:
<223> OTHER INFORMATION: Primer endoSOX2 F

<400> SEQUENCE: 69
cccagcagac ttcacatgt                                                  19

<210> SEQ ID NO 70
<211> LENGTH: 20
<212> TYPE: DNA
<213> ORGANISM: Artificial
<220> FEATURE:
<223> OTHER INFORMATION: Primer endoSOX2 R

<400> SEQUENCE: 70
cctcccattt ccctcgtttt                                                 20

<210> SEQ ID NO 71
<211> LENGTH: 20
<212> TYPE: DNA
<213> ORGANISM: Artificial
<220> FEATURE:
<223> OTHER INFORMATION: Primer endoKLF4 F

<400> SEQUENCE: 71
gatgaactga ccaggcacta                                                 20

<210> SEQ ID NO 72
<211> LENGTH: 20
<212> TYPE: DNA
<213> ORGANISM: Artificial
<220> FEATURE:
<223> OTHER INFORMATION: Primer endoKLF4 R

<400> SEQUENCE: 72
gtgggtcata tccactgtct                                                 20

<210> SEQ ID NO 73
<211> LENGTH: 20
<212> TYPE: DNA
<213> ORGANISM: Artificial
<220> FEATURE:
<223> OTHER INFORMATION: Primer endoMYC F

<400> SEQUENCE: 73
tgcctcaaat tggactttgg                                                 20

<210> SEQ ID NO 74
<211> LENGTH: 22
<212> TYPE: DNA
<213> ORGANISM: Artificial
<220> FEATURE:
<223> OTHER INFORMATION: Primer endoMYC R

<400> SEQUENCE: 74
gattgaaatt ctgtgtaact gc                                              22

```
<210> SEQ ID NO 75
<211> LENGTH: 22
<212> TYPE: DNA
<213> ORGANISM: Artificial
<220> FEATURE:
<223> OTHER INFORMATION: Primer SeV F

<400> SEQUENCE: 75
ggatcactag gtgatatcga gc                                             22

<210> SEQ ID NO 76
<211> LENGTH: 29
<212> TYPE: DNA
<213> ORGANISM: Artificial
<220> FEATURE:
<223> OTHER INFORMATION: Primer SeV R

<400> SEQUENCE: 76
accagacaag agtttaagag atatgtatc                                      29

<210> SEQ ID NO 77
<211> LENGTH: 25
<212> TYPE: DNA
<213> ORGANISM: Artificial
<220> FEATURE:
<223> OTHER INFORMATION: Primer BS OCT4-2 F

<400> SEQUENCE: 77
ttaggaaaat gggtagtagg gattt                                          25

<210> SEQ ID NO 78
<211> LENGTH: 30
<212> TYPE: DNA
<213> ORGANISM: Artificial
<220> FEATURE:
<223> OTHER INFORMATION: Primer BS OCT4-2 R

<400> SEQUENCE: 78
tacccaaaaa acaaataaat tataaaacct                                     30

<210> SEQ ID NO 79
<211> LENGTH: 27
<212> TYPE: DNA
<213> ORGANISM: Artificial
<220> FEATURE:
<223> OTHER INFORMATION: Primer BS OCT4-4 F

<400> SEQUENCE: 79
ggatgttatt aagatgaaga tagttgg                                        27

<210> SEQ ID NO 80
<211> LENGTH: 25
<212> TYPE: DNA
<213> ORGANISM: Artificial
<220> FEATURE:
<223> OTHER INFORMATION: Primer BS OCT4-4 R

<400> SEQUENCE: 80
cctaaactcc ccttcaaaat ctatt                                          25
```

METHOD TO DIRECT DIFFERENTIATION OF PLURIPOTENT STEM CELLS INTO FUNCTIONAL HEART MUSCLE

BACKGROUND OF THE INVENTION

Human pluripotent stem cells (hPSCs) are now widely used to provide a theoretically endless and also large supply of human cardiomyocytes (Kehat et al. J Clin Invest 108, 407-414 (2001); Takahashi et al. Cell 131, 861-872 (2007); Zhang et al., Circ Res 104, e30-41 (2009)). Human cardiomyocytes have been derived from human embryonic stem cells (hESCs) (Thomson et al. Science 282, 1145-1147 (1998)) and induced pluripotent stem cells (hIPSCs) (Takahashi et al., Cell 131, 861-872 (2007)) and have a demonstrated use for multiple purposes including developmental models (Lian et al. Stem Cells 2012 (2012)), drug efficacy and/or safety screening (Schaaf et al. PLoS ONE 6, 20 (2011)), hypertrophy modelling and regenerative applications. Additionally, with recent advances in hIPSC technology, cardiomyocytes exhibiting heritable genetic disease phenotypes can be generated in vitro (Carvajal-Vergara, X. et al. Nature 465, 808-812 (2010); Itzhaki et al., Nature 471, 225-229 (2011); Malan et al. Circ Res (2011); Moretti et al., N Engl J Med 363, 1397-1409 (2010); Yazawa et al. Nature 471, 230-234 (2010)).

It is now widely accepted that the low density 2D culture of biopsy-derived human cardiomyocytes leads to rapid changes in cardiomyocyte phenotype and morphology (Bird et al. Cardiovasc Res 58, 423-434 (2003)) and making it difficult to extrapolate results to the in vivo situation. In order to obtain a cardiomyocyte phenotype more representative of in vivo conditions, cardiac tissue engineering has been used (Eschenhagen et al. FASEB J 11, 683-694 (1997); Zimmermann et al. Biotechnol Bioeng 68, 106-114 (2000); Zimmermann et al. Circ Res 90, 223-230 (2002); Tulloch et al. Circ Res 109, 47-59 (2011); Tiburcy et al. Circ Res 109, 1105-1114 (2011); Eschenhagen et al. Am J Physiol Heart Circ Physiol 303, 11 (2012)) to generate constructs with similar properties to the native heart tissue.

The current ideology of tissue engineering is to generate/isolate the required cell type(s), and seed them into an engineered environment to promote their differentiation and generate in vivo-like tissues. Tissue engineering may therefore be considered as an inefficient process for two reasons, 1) disassociation of a tissue/differentiation culture destroys the extracellular environment thus destroying developmental information (eg. cell-cell interconnectivity, geometric cell positioning, cell-ECM connectivity), this necessitates very large increases in extracellular matrix (ECM) production in order to re-build the environment (Hudson et al. Tissue Eng Part A 17, 2279-2289 (2011)), and 2) the disassociation process is variable between hPSC lines and can lead to considerable cell death.

Other protocols reported in the literature may require modification of the protocol to enable similar cardiomyocyte efficiencies in multiple hPSC lines. However, the inventor's results demonstrate that changes in differentiation protocol may greatly affect the cardiomyocyte phenotype (e.g. it is shown that dorsomorphin may greatly affect the bioengineered heart muscle (BHM)). This may lead to changes in tissue engineered myocardial properties which may mask the effects of different experimental conditions or genetic disease models, therefore care must be taken when using different protocols in different lines.

Some recently published protocols may enable the same protocol to be used for multiple lines, they also produce cardiomyocytes with very high purity. However, pure cardiomyocytes do not facilitate the formation of functional tissue engineered myocardium and both cardiomyocytes and stromal cells are required for the formation of functional tissue engineered myocardium (Naito et al. Circulation 114, 172-78 (2006), Hudson et al. Tissue Eng Part A 17, 2279-2289 (2011)).

Hence, there is a need in the art for methods for producing bioengineered human myocardium, which are capable of overcoming the above disadvantages.

The development of a robust differentiation protocol is a very important step allowing the consistent production of BHM. In this study n>140 BHM in >18 independent experiments were produced and every one exhibited spontaneous beating activity. Additionally, the protocol enables to produce BHM from multiple hPSC lines using the same protocol. In addition, all disassociation steps could be eliminated and hPSCs were differentiated directly into bioengineered myocardium, thus retaining the developmental memory of the tissue, prevent any tissue recreation response and provide a more accurate in vitro model of human myocardial development.

SUMMARY OF THE INVENTION

The present invention relates to a method for producing bioengineered heart muscle from pluripotent stem cells, comprising the steps of (i) cultivating pluripotent stem cells in a basal medium comprising an effective amount of (a) BMP4, Activin A, FGF2, a GSK3-inhibitor, and (b) a serum-free supplement resulting in a final concentration of 0.5-50 mg/ml albumin, 1-100 µg/ml transferrin, 0.1-10 µg/ml ethanol amine, 0.003-0.3 µg/ml sodium selenite, 0.4-40 µg/ml L-Carnitine HCl, 0.1-10 µg/ml Hydrocortisone, 0.05-5 µl/ml Fatty acid supplement, 0.0001-0.1 µg/ml triodo-L-thyronine (T3), thereby inducing mesoderm differentiation of said pluripotent stem cells;

(ii) cultivating the cells obtained in step (i) in a basal medium comprising an effective amount of an inhibitor of the Wnt-signaling pathway and a serum-free supplement as defined in step (i), thereby inducing cardiac differentiation of the cells; and (iii) cultivating the cells obtained in step (ii) in a basal medium comprising an effective amount of a serum-free supplement as defined in step (i), under mechanical stimulation, thereby promoting cardiac maturation.

Carrying out the method disclosed herein human pluripotent stem cell (hPSC)-derived bioengineered heart muscle (BHM) is generated by directed tissue formation of hPSCs in collagen hydrogels. To form BHM, in vivo development was mimicked using a directed serum-free induction protocol causing the tissue to progress through distinct, known developmental stages, through pluripotency, early mesoderm, cardiac progenitor, immature cardiomyocytes and finally to more mature cardiac tissue comprised of 50% cardiomyocytes, with the rest being predominately a stromal cell fraction. The inventors optimized their serum-free BHM protocol and found that individual BHM properties are highly dependent on particular stimuli, thus indicating that multiple exogenous stimuli are required for optimal BHM properties. In the end rhythmically contractile BHM was produced with measurable contractile force, ability for pacing and inotropy in response to increased resting length, calcium concentration and β-adrenergic stimulation. This BHM protocol, without modification, was capable of consistently producing BHM from multiple hPSC lines (in every BHM in every experiment conducted).

The present data suggests that the BHM protocol disclosed herein is a robust, serum-free and reproducible way to produce human myocardium for multiple applications. For example, it is also demonstrated that BHM is a potential model of human myocardium development, and shown that inhibition of BMP signalling leads to a more immature cardiac phenotype with reduced contractile strength.

Accordingly, the present invention is also directed to a BHM produced by the method according to the invention.

Further contemplated is the use of the BHM according to the invention in an in vitro-model for drug toxicity screening. In other words, the present invention is also directed to a method for screening drug toxicity, comprising the step of contacting a BHM according to the invention with a drug to be screened.

Moreover, the present invention is directed to the use of the BHM according to the invention in an in vitro method for testing of cardiac function modulation by pharmacological candidate agents. Thus, also described is a method for testing of cardiac function modulation, comprising the step of contacting a BHM according to the invention with a pharmacological candidate agent.

Finally, the present invention is also directed to the use of the BHM according to the invention as a research tool, as well as to a BHM according to the invention for use in medicine.

DETAILED DESCRIPTION OF THE PREFERRED EMBODIMENTS

A method for producing bioengineered heart muscle from pluripotent stem cells, comprising the steps of
(i) cultivating pluripotent stem cells in a basal medium comprising an effective amount of (a) BMP4, Activin A, FGF2, a GSK3-inhibitor, and (b) a serum-free supplement resulting in a final concentration of 0.5-50 mg/ml albumin, 1-100 µg/ml transferrin, 0.1-10 µg/ml ethanol amine, 0.003-0.3 µg/ml sodium selenite, 0.4-40 µg/ml L-Carnitine HCl, 0.1-10 µg/ml Hydrocortisone, 0.05-5 µl/ml Fatty acid supplement, 0.0001-0.1 µg/ml triodo-L-thyronine (T3), thereby inducing mesoderm differentiation of said pluripotent stem cells;
(ii) cultivating the cells obtained in step (i) in a basal medium comprising an effective amount of an inhibitor of the Wnt-signaling pathway and a serum-free supplement as defined in step (i), thereby inducing cardiac differentiation of the cells; and
(iii) cultivating the cells obtained in step (ii) in a basal medium comprising an effective amount of a serum-free supplement as in (i), under mechanical stimulation, thereby promoting cardiac maturation.

In a preferred embodiment, the pluripotent stem cells are pluripotent stem cells of primate origin, more preferably the pluripotent stem cells are human pluripotent stem cells. Pluripotent stem cells are able to differentiate into every cell type of the body. As such, human pluripotent stem cells offer the unique opportunity to obtain bona fide human heart cells. Currently, the most utilized pluripotent cells are embryonic stem cells (ESC) or induced pluripotent stem cells (iPSC). Human ESC-lines were first established by Thomson and coworkers (Thomson et al., Science 282: 1145-1147 (1998); incorporated herein in its entirety by reference). Human ESC research recently enabled the development of a new technology to reprogram cells of the body into a ES-like cell. This technology was pioneered by Yamanaka and coworkers in 2006 (Takahashi & Yamanaka Cell 126: 663-676 (2006); incorporated herein in its entirety by reference). Resulting induced pluripotent cells (iPSC) show a very similar behavior as ESC and, importantly, are also able to differentiate into every cell of the body. Moreover, it was reported that also parthenogenetic stem cells are likely to be suitable for BHM-production (Didié et al. J Clin Invest. 123, 1285-1298 (2013); incorporated herein in its entirety by reference). Accordingly, the pluripotent stem cells can be selected from embryonic stem cells, induced pluripotent stem cells, and parthenogenetic stem cells. In the context of the present invention, said pluripotent stem cells are however not produced using a process which involves modifying the germ line genetic identity of human beings or which involves use of a human embryo for industrial or commercial purposes.

The basal medium used in step (i), can be selected from DMEM/F12, StemPro, Iscove's medium, αMEM, DMEM, and RPMI. Preferably, the basal medium used in step (i) is RPMI supplemented with pyruvate. However any suitable basal medium may be used in the method. Basal mediums are commercially available or may be prepared according to recipes which are publicly available, e.g. from catalogues of the ATCC. If deemed appropriate, the basal medium may be supplemented with non-essential amino acids. If αMEM is used as the basal medium, the basal medium need not be supplemented additionally with non-essential amino acids. The non-essential amino acids are commercially available as a combined supplement. Such a supplement for example comprises 750 mg/L glycine, 890 mg/L L-alanine, 1320 mg/L L-asparagine, 1330 mg/L L-aspartic acid, 1470 mg/L L-glutamic acid, 1150 mg/L L-proline, and 1050 mg/L L-serine.

As set out above, the basal medium of step (i) comprises an effective amount of BMP4, Activin A, FGF2, and a GSK3-inhibitor. For example, such a basal medium comprises 1-20 ng/ml BMP4, preferably 2-15 ng/ml, more preferably 2.5-10 ng/ml, more preferably 3-8 ng/ml, most preferably 4-6 ng/ml, and even most preferably about 5 ng/ml;
0.1-10 ng/ml FGF2, preferably 1-9 ng/ml, more preferably 2-8 ng/ml, even more preferably 3-7 ng/ml, most preferably 4-6 ng/ml, and even most preferably about 5 ng/ml;
1-20 ng/ml Activin A, preferably 2.5-18 ng/ml, more preferably 5-16 ng/ml, even more preferably 7.5-14 ng/ml, still more preferably 8-12 ng/ml, most preferably 8.5-10 ng/ml, and even most preferably about 9 ng/ml.

The GSK3-inhibitor in the basal medium of step (i) can be selected, for example, from the group consisting of CHIR99021, CHIR98014, SB216763, TWS119, Tideglusib, SB415286, and LY2090314. However, any GSK3-inhibitor suitable in the method of the invention can be applied. In a preferred embodiment, the GSK3-inhibitor in the basal medium of step (i) is CHIR99021.

It will be understood by the skilled person that the concentration of an effective amount of a GSK3-inhibitor varies with the availability and inhibition constant of the inhibitor in question. In the context of the present invention, the term "effective amount" as used herein in the context of a GSK3-inhibitor is intended to mean an enzyme inactivating concentration. For example, in case of CHIR99021, the basal medium in step (i) comprises 0.1-10 µM CHIR99021, preferably 0.2-9 µM, more preferably 0.3-8 µM, even more preferably 0.4-7 µM, still more preferably 0.5-6 µM, more preferably 0.6-5 µM, more preferably 0.7-4 µM, more preferably 0.8-3 µM, most preferably 0.9-2 µM, and even most preferably about 1 µM CHIR99021. It will be understood that an effective concentration of any receptor/enzyme agonist or inhibitor varies with the availability and biological activity of the respective compound. The serum-free supplement applied in step (i), (ii) and (iii) of the method is formulated to result in a final concentration of 0.5-50 mg/ml albumin (preferably 1-40 mg/ml, more preferably 2-30 mg/ml, still more preferably 3-20 mg/ml, most preferably 4-10 mg/ml, and even most preferably 4.5-7.5 mg/ml such as about 5 mg/ml), 1-100 µg/ml transferrin (preferably 2-90 µg/ml, more preferably 3-80 µg/ml, even more preferably 4-70 µg/ml, still more preferably 5-60 µg/ml, more preferably 6-50 µg/ml, more preferably 7-40 µg/ml, more preferably 8-30 µg/ml, more preferably 9-20 µg/ml, such as about 10 µg/ml),
0.1-10 µg/ml ethanol amine (preferably 0.2-9 µg/ml, more preferably 0.3-8 µg/ml, even more preferably 0.4-7 µg/ml, still more preferably 0.5-6 µg/ml, more preferably 0.6-5 µg/ml, more preferably 0.7-4 µg/ml, more preferably 0.8-3 µg/ml, more preferably 1-2.5 µg/ml, such as about 2 µg/ml),
0.003-0.3 µg/ml sodium selenite (preferably 0.005-0.2 µg/ml, more preferably 0.01-0.1 µg/ml, even more preferably 0.02-0.05 µg/ml, and most preferably about 0.03 µg/ml, such as about 0.032 µg/ml),
0.4-40 µg/ml L-Carnitine HCl (preferably 0.5-30 µg/ml, more preferably 1-20 µg/ml, even more preferably 2-10 µg/ml, most preferably 3-5 µg/ml, and even most preferably about 4 µg/ml),
0.1-10 µg/ml Hydrocortisone (preferably 0.2-9 µg/ml, more preferably 0.3-8 µg/ml, even more preferably 0.4-7 µg/ml, still more preferably 0.5-6 µg/ml, more preferably 0.6-5 µg/ml, more preferably 0.7-4 µg/ml, more preferably 0.8-3 µg/ml, more preferably 0.9-2 µg/ml, such as about 1 µg/ml),
0.05-5 µl/ml Fatty acid supplement (preferably 0.1-4 µl/ml, more preferably 0.2-3 µl/ml, even more preferably 0.3-3 µl/ml, most preferably 0.4-2 µl/ml, and even most preferably 0.45-1 µl/ml, such as about 0.5 µl/ml), and
0.0001-0.1 µg/ml triodo-L-thyronine (T3) (preferably 0.001-0.01 µg/ml, more preferably 0.002-0.0075 µg/ml, even more preferably 0.003-0.005 µg/ml, and most preferably about 0.004 µg/ml).

In addition, the serum-free supplement may further comprise one or more components selected from the group consisting of vitamin A, D-galactose, L-carnitine, linoleic acid, linolenic acid, progesterone, and putrescine. These components are conducive for the viability of the cells. Suitable concentrations of the respective components are known to the skilled person or can be easily determined using routine measures.

The serum-free supplement referred to in step (i) is also commercially available. For example, B27® supplement or B27® supplement minus insulin can be used. In a preferred embodiment, the B27® supplement or B27® supplement minus insulin used in step (i) of the above method is applied in an amount of 0.1-10% B27® or B27® minus insulin, preferably 0.5-8%, more preferably 1-6%, even more preferably 1.5-4%, and most preferably about 2% B27® or B27® minus insulin.

As demonstrated in the examples below, it has been proven advantageous to include an effective amount of ascorbic acid or a salt or a derivative thereof into the basal medium of step (i). In a preferred embodiment, the basal medium of step (i) comprises 10-1000 µM, preferably 50-400 µM, more preferably 100-300 µM, even more preferably 150-250 µM, and most preferably about 200 µM of ascorbic acid or a salt or a derivative thereof. The ascorbic acid may be delivered in the free form or as a salt. Since ascorbate is the active ingredient, any salt or derivative of ascorbic acid may be used, which provides the ascorbate to the cells, provided the counter ion has no detrimental effect on the cells. As shown in the examples, one suitable salt or derivative of ascorbic acid is ascorbate-2-phosphate.

The length of step (i) and the concentration of factors such as BMP4, Activin A, FGF2, and the GSK3-inhibitor may be optimized by monitoring the efficiency of induction of mesoderm differentiation. This can be achieved by monitoring the expression of cell surface or pluripotency markers, i.e. by (a) a decrease of TRA-1-60 and OCT4 positive cells (pluripotent stem cells) and (b) an increase of MIXL1 and Mesp1 positive cells (mesoderm) (see also FIG. 4f herein).

Briefly, cells are fixed using ethanol, blocked using standard protocols, and then stained with primary antibodies directed against TRA-1-60, OCT4, MIXL1 and/or Mesp1 (cf. Table 2 below) in blocking buffer for 45 min, optionally followed by secondary antibodies (if the primary antibody is not fluorescence labelled) in blocking buffer and Hoechst for 30 min at 4° C. (cf. Table 2 below). A BD LSRII is used for flow cytometry analysis (BD Biosystems). For live cells populations are gated based on forward-side scatter profiles. BD FACSDiva Software (BD Bioscience) or Cyflologic v1.2.1 (Cyflo Ltd) are used for analysis. Induction of mesoderm differentiation is indicated if (a) less than 50%, preferably less than 40%, more preferably less than 30%, even more preferably less than 20%, most preferably less than 10%, and even most preferably less than 5% of the cells of the live cells population are positive for TRA-1-60; and/or less than 50%, preferably less than 40%, more preferably less than 30%, even more preferably less than 20%, most preferably less than 10%, and even most preferably less than 5% of the cells of the live cells population are positive for OCT4; and (b) more than 20%, preferably more than 30%, more preferably more than 40%, even more preferably more than 50%, and most preferably more than 60%, of the cells of the live cells population are positive for MIXL1; and/or more than 20%, preferably more than 30%, more preferably more than 40%, even more preferably more than 50%, and most preferably more than 60% of the cells of the live cells population are positive for Mesp1.

Usually, step (i) is carried out for 48-96 h. Preferably, step (i) is carried out for 60-84 h, and more preferably step (i) is carried out for 66-78 h.

The basal medium used in step (ii), can be selected from DMEM/F12, StemPro, Iscove's medium, αMEM, DMEM, and RPMI. Preferably, the basal medium used in step (ii) is RPMI supplemented with pyruvate. However any suitable basal medium may be used in the method.

If deemed appropriate, the basal medium of step (ii) may be supplemented with non-essential amino acids. If αMEM is used as the basal medium in step (ii), the basal medium need not be supplemented additionally with non-essential amino acids. The non-essential amino acids are commercially available as a combined supplement. Such a supplement for example comprises 750 mg/L glycine, 890 mg/L L-alanine, 1320 mg/L L-asparagine, 1330 mg/L L-aspartic acid, 1470 mg/L L-glutamic acid, 1150 mg/L L-proline, and 1050 mg/L L-serine.

The basal medium in step (ii) may be independently selected from the basal medium applied in step (i). However, in a preferred embodiment, the basal medium in steps (i) and (ii) is the same.

The inhibitor of the Wnt-signaling pathway in the basal medium of step (ii) may be any inhibitor of the Wnt-signaling pathway, which can be suitably applied in the method of the invention. Preferably, said inhibitor of the Wnt-signaling pathway is selected from the group consisting of IWP4, IWP2, IWR-1, IWP1, IWP3, IWR-2, IWR3, IWR-4, IWR-5, XAV939, DKK1, quercetin, ICG-001, pyrvinium, CCT031374, iCRT3,5,14, CPG049090, and NC043. More preferably said inhibitor of the Wnt-signaling pathway is selected from the group consisting of IWP4, IWP2, IWR-1, IWP1, IWP3, IWR-2, IWR-3, IWR-4, IWR-5, XAV939, DKK1. As demonstrated in the examples below, one particularly useful inhibitor of the Wnt-signaling pathway in the basal medium of step (ii) is IWP4.

The serum-free supplement referred to in step (ii) is as defined for step (i) above. The serum-free supplements applied in step (i) and (ii) may be the same or not. Likewise, B27® supplement or B27® supplement minus insulin can be used in step (ii). In a preferred embodiment, the B27® supplement or B27® supplement minus insulin used in step (ii) of the above method is applied in an amount of 0.1-10% B27® or B27® minus insulin, preferably 0.5-8%, more preferably 1-6%, even more preferably 1.5-4%, and most preferably about 2% B27® or B27® minus insulin.

It will be understood by the skilled person that the concentration of an effective amount of an inhibitor of the Wnt-signaling pathway varies with the availability and inhibition constant of the inhibitor in question. For example, in case of IWP4, the basal medium of step (ii) may comprise 0.1-10 µM IWP4, preferably 1-9 µM, more preferably 2-8 µM, even more preferably 3-7 µM, still more preferably 4-6 µM, and most preferably about 5 µM IWP4. It will be understood that an effective concentration of any receptor/enzyme agonist or inhibitor varies with the availability and biological activity of the respective compound.

As demonstrated in the examples below, it has been proven advantageous to include an effective amount of ascorbic acid or a salt or a derivative thereof into the basal medium of step (ii). In a preferred embodiment, the basal medium of step (ii) comprises 10-1000 µM, preferably 50-400 µM, more preferably 100-300 µM, even more preferably 150-250 µM, and most preferably about 200 µM of ascorbic acid or a salt or a derivative thereof. The ascorbic acid may be delivered in the free form or as a salt. Since ascorbate is the active ingredient, any salt or derivative of ascorbic acid may be used, which provides the ascorbate to the cells, provided the counter ion has no detrimental effect on the cells. As shown in the examples, one suitable salt or derivative of ascorbic acid for use in the basal medium in step (ii) is ascorbate-2-phosphate.

The length of step (ii) and the concentration of the remaining constituents such as the inhibitor of the Wnt-signaling pathway may be optimized by monitoring the efficiency of induction of cardiac differentiation of the cells. This can be achieved by monitoring the expression of differentiation markers, i.e. by an increase of Nkx2.5 and actinin.

Briefly, cells are fixed using ethanol, blocked, and then stained with primary antibodies directed against Nkx2.5 and/or actinin (cf. Table 2 below) in blocking buffer for 45 min, optionally followed by secondary antibodies (if the primary antibody is not fluorescence labelled) in blocking buffer and Hoechst for 30 min at 4° C. (cf. Table 2 below). A BD LSRII is used for flow cytometry analysis (BD Biosystems). For live cells populations are gated based on forward-side scatter profiles. BD FACSDiva Software (BD Bioscience) or Cyflologic v1.2.1 (Cyflo Ltd) are used for analysis. Induction of cardiac differentiation is indicated if more than 20%, preferably more than 30%, more preferably more than 40%, even more preferably more than 50%, and most preferably more than 60%, of the cells of the live cells population are positive for Nkx2.5; and/or more than 20%, preferably more than 30%, more preferably more than 40%, even more preferably more than 50%, and most preferably more than 60% of the cells of the live cells population are positive for actinin (see also FIGS. 4d and 4f herein).

Usually, step (ii) is carried out for 8-12 days. Preferably, step (ii) is carried out for 9-11 days, and most preferably step (ii) is carried out for 10 days.

The basal medium used in step (iii), can be selected from DMEM/F12, StemPro, Iscove's medium, αMEM, DMEM, and RPMI. Preferably, the basal medium used in step (iii) is RPMI supplemented with pyruvate. However any suitable basal medium may be used in the method.

If deemed appropriate, the basal medium of step (iii) may be supplemented with non-essential amino acids. If αMEM is used as the basal medium in step (iii), the basal medium need not be supplemented additionally with non-essential amino acids. The non-essential amino acids are commercially available as a combined supplement. Such a supplement for example comprises 750 mg/L glycine, 890 mg/L L-alanine, 1320 mg/L L-asparagine, 1330 mg/L L-aspartic acid, 1470 mg/L L-glutamic acid, 1150 mg/L L-proline, and 1050 mg/L L-serine.

The basal medium in step (iii) may be independently selected from the basal medium applied in steps (i) and/or (ii). However, in a preferred embodiment, the basal medium in steps (ii) and (iii) is the same. More preferably, the basal medium in steps (i), (ii) and (iii) is the same.

As demonstrated in the examples below, it has been proven advantageous to include an effective amount of ascorbic acid or a salt or a derivative thereof into the basal medium of step (iii). In a preferred embodiment, the basal medium of step (iii) comprises 10-1000 µM, preferably 50-400 µM, more preferably 100-300 µM, even more preferably 150-250 µM, and most preferably about 200 µM of ascorbic acid or a salt or a derivative thereof. The ascorbic acid may be delivered in the free form or as a salt. Since ascorbate is the active ingredient, any salt or derivative of ascorbic acid may be used, which provides the ascorbate to the cells, provided the counter ion has no detrimental effect on the cells. As shown in the examples, one suitable salt or derivative of ascorbic acid for use in the basal medium in step (iii) is ascorbate-2-phosphate.

The serum-free supplement referred to in step (iii) is a serum-free supplement as defined for step (i) above. The serum-free supplements applied in steps (i), (ii) and (iii) may be the same or not. Likewise, B27® supplement or B27® supplement minus insulin can be used in step (iii). In a preferred embodiment, the B27® supplement or B27® supplement minus insulin used in step (iii) of the above method is applied in an amount of 0.1-10% B27® or B27® minus insulin, preferably 0.5-8%, more preferably 1-6%, even more preferably 1.5-4%, and most preferably about 2% B27® or B27® minus insulin.

The basal medium of step (iii) further comprises an effective amount of TGFβ1. For example, the basal medium of step (iii) may comprise 0.1-10 ng/ml TGFβ1, preferably 0.2-9 ng/ml, more preferably 0.3-8 ng/ml, even more preferably 0.4-7 ng/ml, still more preferably 0.5-6 ng/ml, more preferably 0.6-5 ng/ml, more preferably 0.7-4 ng/ml, more preferably 0.8-3 ng/ml, most preferably 0.9-2 ng/ml, and even most preferably about 1 ng/ml TGFβ1.

As shown in the examples, it is advantageous for cardiac maturation if the basal medium of step (iii) does not comprise an effective amount of FGF2. In contrast thereto, calcium has been shown to improve cardiac maturation. Accordingly, in a preferred embodiment, the basal medium of step (iii) comprises 0.5-3 mM $Ca^{2+}$, preferably 0.5-2.75 mM $Ca^{2+}$, more preferably 1-2.25 mM $Ca^{2+}$, even more preferably 1-1.5 mM $Ca^{2+}$, and most preferably about 1.2 mM $Ca^{2+}$.

Usually, step (iii) of the method of the invention is carried out under mechanical stimulation, e.g. on a stretch device, as generally known in the art. Preferably, the stretch device applies a static, phasic or dynamic stretch to the BHM. More specifically, mechanical stretching can be (a) static, (b) dynamic, or (c) flexible against a resilient load. Preferably, the mechanical stimulation in step (iii) is dynamic mechanical stimulation or static stretch. In a more preferred embodiment, the mechanical stimulation in step (iii) is dynamic mechanical stimulation against a resilient load to facilitate auxotonic contractions.

Whether cardiac maturation is promoted can be tested by optical inspection for spontaneous or electrically stimulated contractions. Preferably, cardiac maturation is monitored by an isometric contraction experiment, wherein a twitch force development of >0.01 mN is indicative for cardiac maturation.

Briefly, contraction experiments are performed in organ baths at 37° C. under constant bubbling with 5% $CO_2$ and 95% $O_2$ to maintain a physiological pH in Tyrode's solution containing (all in mM): 120 NaCl, 1 $MgCl_2$, 0.2 $CaCl_2$, 5.4 KCl, 22.6 $NaHCO_3$, 4.2 $NaH_2PO_4$, 5.6 glucose and 0.56 ascorbate. Calcium is adjusted using a 0.2 M calcium chloride solution. All BHM are analysed at 3 Hz with 5 ms square pulses of 200 mA electrical current in order to pace at approximately the embryonic heart rate. Stimulation frequency is altered to confirm proper force-frequency response (Bowditch mechanism). BHM are mechanically stretched at intervals of 125 μm until the maximum twitch force is observed (force-length response; Frank-Starling mechanism).

Usually, step (iii) is carried out for at least 72 h. Although there is no particular upper limit for the length of step (iii), said step is usually carried out for less than 100 days. In specific embodiments, step (iii) may be carried out for 4-50 days, such as for about 15 days.

Step (i) of the method of the invention may be preceded by a seeding step, wherein said pluripotent stem cells are seeded in a ratio of (2.5-6×10$^6$ cells/1 mg collagen)/1 ml medium in a suitable mould. Preferably, the seeding step is carried out 18-30 h prior to step (i).

The medium used in the seeding step usually comprises 0.2-2 mg/ml collagen (preferably 0.3-1.9 mg/ml, more preferably 0.4-1.8 mg/ml, even more preferably 0.4-1.7 mg/ml, still more preferably 0.5-1.6 mg/ml, more preferably 0.6-1.5 mg/ml, more preferably 0.7-1.4 mg/ml, more preferably 0.8-1.3 mg/ml, more preferably 0.9-1.2 mg/ml, such as about 1 mg/ml). The collagen is preferably of medical grade and selected from the group consisting of collagen type I, collagen type III, collagen type V, and a mixture thereof. In a more preferred embodiment, at least 90% of said collagen is collagen type I. However, said collagen may also further comprises one or more extracellular matrix components selected from the group consisting of elastin, laminin, entactin, nidogen, proteoglycan, and fibronectin. Usually, the exact composition of the collagen will depend on the origin, from where it is derived from. The collagen is preferably of human origin, but bovine or porcine origin, or marine origin, such as from algae or fish origin, is also contemplated. Alternatively, recombinant collagen may also be used.

In order to achieve suitable cell densities, for some pluripotent cell lines it may be helpful to supplement the medium used in the seeding step with a ROCK-inhibitor. Therefore, in a preferred embodiment, the medium used in the seeding step further comprises a ROCK-inhibitor. The ROCK-inhibitor may be any ROCK-inhibitor, which can be suitably applied in the method of the invention. Preferably, said ROCK inhibifor is selected from Y27632, H-1152P, Thiazovivin, Fasudil, Hydroxyfasudil, GSK429286A, and RKI-1447, preferably selected from Y27632, H-1152P, Thiazovivin, Fasudil, Hydroxyfasudil, and more preferably the ROCK inhibitor is selected from Y27632 or H-1152P. As demonstrated in the examples below, one particularly useful ROCK-inhibitor is Y27632.

It will be understood by the skilled person that the concentration of an effective amount of a ROCK-inhibitor varies with the availability and inhibition constant of the inhibitor in question. For example, in case of Y27632, the medium used in the seeding step may comprise 1-50 μM, preferably 2.5-40 μM, more preferably 5-30 μM, even more preferably 7.5-20 μM, most preferably 8-12 μM, and most preferably about 10 μM Y27632.

It will be understood that an effective concentration of any receptor/enzyme agonist or inhibitor varies with the availability and biological activity of the respective compound.

Apart from the above disclosed method, the invention further relates to a BHM produced by said method. Despite the increased maturity observed in our BHM protocol, it should also be noted that the BHM is still a relatively immature tissue. Compared to adult heart tissue the BHM still has an inferior β-MHC/α-MHC ratio, and low but still retained expression of progenitor genes (e.g. ISL1). However, prolonged culture under appropriate culture conditions with biophysical stimulation may further increase maturity. There is already morphological evidence suggesting that this may also be the case in the BHM system.

The BHM obtained by the method disclosed herein exhibits the following characteristics: It can be paced at multiple frequencies up to at least 3 Hz, exhibits a calcium $EC_{50}$ of higher than 0.2 mM being preferably in the physiological range 4-8 mM, and a twitch tension of more than 200 μN. The twitch tension is increased in response to increased resting length and resting tension. In response to 1 μM isoprenaline, the BHM exhibits an inotropic response of more than 40 μN under paced conditions at 0.6 mM calcium, preferably more than 45 μN, more preferably more than 50 μN.

Briefly, all contraction experiments are performed in organ baths at 37° C. and physiological pH in Tyrode's solution containing (all in mM): 120 NaCl, 1 $MgCl_2$, 0.2 $CaCl_2$, 5.4 KCl, 22.6 $NaHCO_3$, 4.2 $NaH_2PO_4$, 5.6 glucose and 0.56 ascorbate. Calcium is adjusted using a 0.2 M calcium chloride solution. All BHM are analysed at 3 Hz with 5 ms square pulses of 200 mA electrical current in order to pace at approximately the embryonic heart rate. Stimulation frequency is altered to confirm proper force-frequency response (Bowditch mechanism). BHM are mechanically stretched at intervals of 125 μm until the maximum twitch force is observed at 2 mM calcium (Frank-Starling mechanism). Subsequently, BHM are subjected to different calcium concentrations (0.2, 0.4, 0.8, 1.2, 1.6, 2.0, 2.4 mM) and the twitch force is recorded. For isoprenaline experiments the calcium concentration is adjusted to 0.6 mM and subsequently the isoprenaline concentration is adjusted to 1 μM.

Another characteristic of the BHM obtained by the method disclosed herein is that it comprises CD90$^+$ stromal cells. Expression of CD90 can be determined using flow cytometry. Briefly, cells are fixed using ethanol, blocked, and then stained with primary antibodies directed against CD90 (cf. Table 2 below) in blocking buffer for 45 min, optionally followed by secondary antibodies (if the primary antibody is not fluorescence labelled) in blocking buffer and Hoechst for 30 min at 4° C. (cf. Table 2 below). A BD LSRII is used for flow cytometry analysis (BD Biosystems). For live cells populations are gated based on forward-side scatter profiles. BD FACSDiva Software (BD Bioscience) or Cyflologic v1.2.1 (Cyflo Ltd) are used for analysis.

The BHM may provide a good model system for investigating mechanisms driving maturation in a serum-free environment, and we have already demonstrated that with increased culture periods maturity may be increased (we showed increase isoprenaline sensitivity and improve tissue morphology). The capability of long term BHM culture without loss of function (at least 63 days) also suggests that long term pharmacological safety and efficacy experiments are possible. Hence, in a preferred embodiment, the BHM obtained by the method disclosed herein can be maintained for at least 63 days.

Using the traditional approach of differentiation followed by tissue engineering the differentiation cultures require extensive digestion protocols in order to yield single cell/small clumps required for cardiac tissue engineering applications. These digestion protocols destroy the extracellular environment and spatial distribution formed during development and may hence have a difficult to control inhibitory effect on the cardiac differentiation protocol.

Using the BHM as a model we demonstrated that factors affecting early development (ASC-2-P, dorsomorphin) and later development (mechanical stimulation, FGF2, TGFβ1, and calcium concentration) had a profound impact on BHM function and properties. Therefore, our BHM protocol may be a useful tool in the study of developmental processes not only governing cardiogenesis, but also tissue formation and properties.

Accordingly, the BHM obtained by the method disclosed herein can be suitably used as a research tool. For example, the use of the BHM obtained by the method disclosed herein in an in vitro-model for drug toxicity screening is contemplated. In other words, a method for screening drug toxicity is contemplated, comprising the step of contacting a BHM obtained by the method disclosed herein with a drug to be screened. Alternatively, the BHM obtained by the method disclosed herein may be used in an in vitro method for testing of cardiac function modulation by pharmacological candidate agents. Thus, also described is a method for testing of cardiac function modulation, comprising the step of contacting a BHM according to the invention with a pharmacological candidate agent.

Finally, the BHM obtained by the method disclosed herein can be used in medicine. Merely as an example, it is contemplated that the BHM obtained by the method disclosed herein can be advantageously used in heart repair.

The invention is further described by the following embodiments:

1. A method for producing bioengineered heart muscle from pluripotent stem cells, comprising the steps of
   (i) cultivating pluripotent stem cells in a basal medium comprising an effective amount of (a) BMP4, Activin A, FGF2, a GSK3-inhibitor, and (b) a serum-free supplement resulting in a final concentration of 0.5-50 mg/ml albumin, 1-100 µg/ml transferrin, 0.1-10 µg/ml ethanol amine, 0.003-0.3 µg/ml sodium selenite, 0.4-40 µg/ml L-Carnitine HCl, 0.1-10 µg/ml Hydrocortisone, 0.05-5 µl/ml Fatty acid supplement, 0.0001-0.1 µg/ml triodo-L-thyronine (T3), thereby inducing mesoderm differentiation of said pluripotent stem cells;
   (ii) cultivating the cells obtained in step (i) in a basal medium comprising an effective amount of an inhibitor of the Wnt-signaling pathway and a serum-free supplement as in (i), thereby inducing cardiac differentiation of the cells; and
   (iii) cultivating the cells obtained in step (ii) in a basal medium comprising an effective amount of a serum-free supplement as in (i), under mechanical stimulation, thereby promoting cardiac maturation.
2. The method of embodiment 1, wherein the pluripotent stem cells are pluripotent stem cells of primate origin, preferably human pluripotent stem cells.
3. The method of embodiment 1 or 2, wherein the pluripotent stem cells are selected from embryonic stem cells, induced pluripotent stem cells, and parthenogenetic stem cells.
4. The method of any one of embodiment 1-3, wherein the basal medium, of step (i) comprises 10-1000 µM, preferably 50-400 µM, more preferably 100-300 µM, even more preferably 150-250 µM, and most preferably about 200 µM of ascorbic acid or a salt or a derivative thereof.
5. The method of embodiment 4, wherein the salt or derivative of ascorbic acid is ascorbate-2-phosphate.
6. The method of any one of embodiment 1-5, wherein step (i) is carried out for 48-96 h, preferably wherein step (i) is carried out for 60-84 h, most preferably wherein step (i) is carried out for 66-78 h.
7. The method of any one of embodiment 1-6, wherein the basal medium in step (i) comprises 1-20 ng/ml BMP4, preferably 2-15 ng/ml, more preferably 2.5-10 ng/ml, more preferably 3-8 ng/ml, most preferably 4-6 ng/ml, and even most preferably about 5 ng/ml.
8. The method of any one of embodiment 1-7, wherein the basal medium in step (i) comprises 0.1-10 ng/ml FGF2, preferably 1-9 ng/ml, more preferably 2-8 ng/ml, even more preferably 3-7 ng/ml, most preferably 4-6 ng/ml, and even most preferably about 5 ng/ml.
9. The method of any one of embodiment 1-8, wherein the basal medium in step (i) comprises 1-20 ng/ml Activin A, preferably 2.5-18 ng/ml, more preferably 5-16 ng/ml, even more preferably 7.5-14 ng/ml, still more preferably 8-12 ng/ml, most preferably 8.5-10 ng/ml, and even most preferably about 9 ng/ml.
10. The method of any one of embodiment 1-9, wherein the GSK3-inhibitor in the basal medium of step (i) is selected from the group consisting of CHIR99021, CHIR98014, SB216763, TWS119, Tideglusib, SB415286, and LY2090314.
11. The method of embodiment 10, wherein the GSK3-inhibitor in the basal medium of step (i) is CHIR99021.
12. The method of embodiment 11, wherein the basal medium in step (i) comprises 0.1-10 µM CHIR99021, preferably 0.2-9 µM, more preferably 0.3-8 µM, even more preferably 0.4-7 µM, still more preferably 0.5-6 µM, more preferably 0.6-5 µM, more preferably 0.7-4 µM, more preferably 0.8-3 µM, most preferably 0.9-2 µM, and even most preferably about 1 µM CHIR99021.
13. The method of any one of embodiment 1-12, wherein the serum-free supplement in step (i) comprises 0.1-10% B27 or B27 minus insulin, preferably 0.5-8%, more preferably 1-6%, even more preferably 1.5-4%, and most preferably about 2% B27 or B27 minus insulin.
14. The method of any one of embodiment 1-13, wherein the basal medium used in step (i), is DMEM/F12, StemPro, Iscove's medium, αMEM, DMEM, and RPMI.
15. The method of claim 14, wherein the basal medium used in step (i) is RPMI supplemented with pyruvate.
16. The method of any one of embodiment 1-15, wherein the inhibitor of the Wnt-signaling pathway in the basal medium of step (ii) is selected from the group consisting of IWP4, IWP2, IWR-1, IWP1, IWP3, IWR-2, IWR-3, IWR-4, IWR-5, XAV939, DKK1, quercetin, ICG-001, pyrvinium, iCRT-3,5,14, CPG049090, NC043; preferably selected from the group consisting of IWP4, IWP2, IWR-1, IWP1, IWP3, IWR-2, IWR-3, IWR-4, IWR-5, XAV939, DKK1.

17. The method of embodiment 16, wherein the inhibitor of the Wnt-signaling pathway in the basal medium of step (ii) is IWP4.

18. The method of embodiment 17, wherein the basal medium of step (ii) comprises 0.1-10 µM IWP4, preferably 1-9 µM, more preferably 2-8 µM, even more preferably 3-7 µM, still more preferably 4-6 µM, and most preferably about 5 µM IWP4.

19. The method of any one of embodiment 1-18, wherein the basal medium of step (ii) comprises 10-1000 µM, preferably 50-400 µM, more preferably 100-300 µM, even more preferably 150-250 µM, and most preferably about 200 µM of ascorbic acid or a salt or a derivative thereof.

20. The method of embodiment 19, wherein the salt or derivative of ascorbic acid is ascorbate-2-phosphate.

21. The method of any one of embodiment 1-20, wherein step (ii) is carried out for 8-12 days, preferably wherein step (ii) is carried out for 9-11 days, most preferably wherein step (ii) is carried out for 10 days.

22. The method of any one of embodiment 1-21, wherein the serum-free supplement in step (ii) comprises 0.1-10% B27 or B27 minus insulin, preferably 0.5-8%, more preferably 1-6%, even more preferably 1.5-4%, and most preferably about 2% B27 or B27 minus insulin.

23. The method of any one of embodiment 1-22, wherein the basal medium used in step (ii), is DMEM/F12, StemPro, Iscove's medium, αMEM, DMEM, and RPMI.

24. The method of embodiment 23, wherein the basal medium used in step (ii) is RPMI supplemented with pyruvate.

25. The method of any one of embodiment 1-24, wherein the basal medium of step (iii) further comprises 10-1000 µM, preferably 50-400 µM, more preferably 100-300 µM, even more preferably 150-250 µM, and most preferably about 200 µM of ascorbic acid or a salt or a derivative thereof.

26. The method of embodiment 25, wherein the salt or derivative of ascorbic acid is ascorbate-2-phosphate.

27. The method of any one of embodiment 1-26, wherein step (iii) is carried out for at least 72 h, preferably wherein step (iii) is carried out for less than 100 days, more preferably wherein step (iii) is carried out for 4-50 days, and most preferably wherein step (iii) is carried out for about 15 days.

28. The method of any one of embodiment 1-27, wherein the serum-free supplement in step (iii) comprises 0.1-10% B27 or B27 minus insulin, preferably 0.5-8%, more preferably 1-6% 7, even more preferably 1.5-4%, and most preferably about 2% B27 or B27 minus insulin.

29. The method of any one of embodiment 1-28, wherein the basal medium used in step (iii), is DMEM/F12, StemPro, Iscove's medium, αMEM, DMEM, and RPMI.

30. The method of embodiment 29, wherein the basal medium used in step (i) is RPMI supplemented with pyruvate.

31. The method of any one of embodiment 1-30, wherein the basal medium of step (iii) further comprises 0.1-10 ng/ml TGFβ1, preferably 0.2-9 ng/ml, more preferably 0.3-8 ng/ml, even more preferably 0.4-7 ng/ml, still more preferably 0.5-6 ng/ml, more preferably 0.6-5 ng/ml, more preferably 0.7-4 ng/ml, more preferably 0.8-3 ng/ml, most preferably 0.9-2 ng/ml, and even most preferably about 1 ng/ml TGFβ1.

32. The method of any one of embodiment 1-31, wherein the basal medium of step (iii) does not comprise an effective amount of FGF2.

33. The method of any one of embodiment 1-32, wherein the basal medium of step (iii) comprises 0.5-3 mM $Ca^{2+}$, preferably 0.5-2.75 mM $Ca^{2+}$, more preferably 1-2.25 mM $Ca^{2+}$, even more preferably 1-1.5 mM $Ca^{2+}$, and most preferably about 1.2 mM $Ca^{2+}$.

34. The method of any one of embodiment 1-33, wherein the mechanical stimulation in step (iii) is dynamic mechanical stimulation or static stretch.

35. The method of embodiment 34, wherein the mechanical stimulation in step (iii) is dynamic mechanical stimulation.

36. The method of any one of embodiment 1-35, comprising prior to step (i) a seeding step, wherein said pluripotent stem cells are seeded in a ratio of $(2.5-6\times10^6$ cells/1 mg collagen)/1 ml medium in a suitable mould.

37. The method of embodiment 36, wherein the collagen is collagen I.

38. The method of any one of embodiment 36-37, wherein said collagen is of human origin, bovine origin, or marine origin.

39. The method of any one of embodiment 36-38, wherein the medium used in the seeding step further comprises a ROCK-inhibitor.

40. The method of embodiment 39, wherein the ROCK inhibitor is selected from Y27632, H-1152P, Thiazovivin, Fasudil, Hydroxyfasudil, GSK429286A, and RKI-1447, preferably selected from Y27632, H-1152P, Thiazovivin, Fasudil, Hydroxyfasudil, and more preferably the ROCK inhibitor is Y27632 or H-1152P, and most preferably the ROCK inhibitor is Y27632.

41. The method of embodiment 40, wherein the medium used in the seeding step comprises 1-50 µM, preferably 2.5-40 µM, more preferably 5-30 µM, even more preferably 7.5-20 µM, most preferably 8-12 µM, and most preferably about 10 µM Y27632.

42. The method of any one of embodiment 36-41, wherein the seeding step is carried out 18-30 h prior to step (i).

43. A bioengineered human myocardium (BHM) produced by the method according to any one of embodiment 1-42.

44. The BHM of embodiment 43, which can be paced at multiple frequencies of up to at least 3 Hz.

45. The BHM of embodiment 43 or 44, which exhibits an increased twitch tension in response to increased resting length and resting tension.

46. The BHM of any one of embodiment 43-45, which exhibits a calcium $EC_{50}$ higher than 0.2 mM.

47. The BHM of any one of embodiment 43-46, which exhibits a twitch tension of more than 200 µN.

48. The BHM of any one of embodiment 43-47, which exhibits an inotropic response to 1 µM isoprenaline of more than 40 µN under paced conditions at 0.6 mM calcium, preferably more than 45 µN, more preferably more than 50 µN.

49. The BHM of any one of embodiment 43-48, which comprises cardiomyocytes and CD90+ stromal cells.

50. The BHM of any one of embodiment 43-49, which can be maintained for at least 62 days.

51. Use of the bioengineered human myocardium (BHM) according to any one of embodiment 43-50 in an in vitro-model for drug toxicity screening.

52. Use of the bioengineered human myocardium (BHM) according to any one of embodiment 43-50 in an in vitro method for testing of cardiac function modulation by pharmacological candidate agents.

53. Use of the bioengineered human myocardium (BHM) according to any one of embodiment 43-50 as a research tool.

54. The bioengineered human myocardium (BHM) according to any one of embodiment 43-50 for use in medicine.

55. The bioengineered human myocardium (BHM) according to any one of embodiment 43-50 for use in heart repair.

The following examples are meant to further illustrate, but not limit the invention. The examples comprise various technical features, and it will be appreciated that the invention also relates to combinations of the technical features presented in this exemplifying section.

Figure 10:
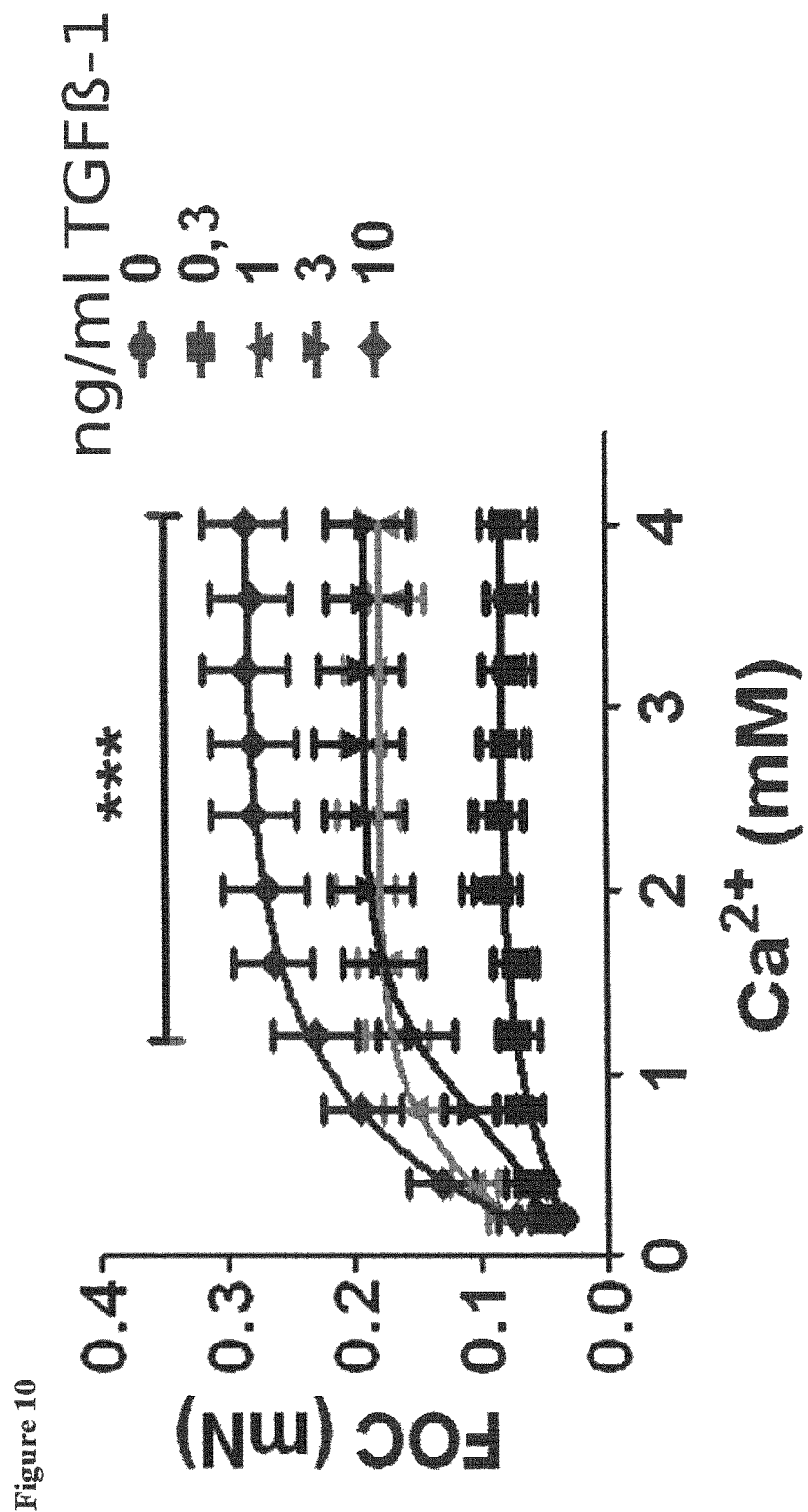

FIG. 10: Supplementation of the culture medium with TGFβ-1 during the cardiac maturation phase enhances contractile function of BHM (FOC: force of contraction) in a concentration dependent manner (0.3-10 ng/ml tested; n=5-7 BHMs/condition).

EXAMPLES

Figure 1:
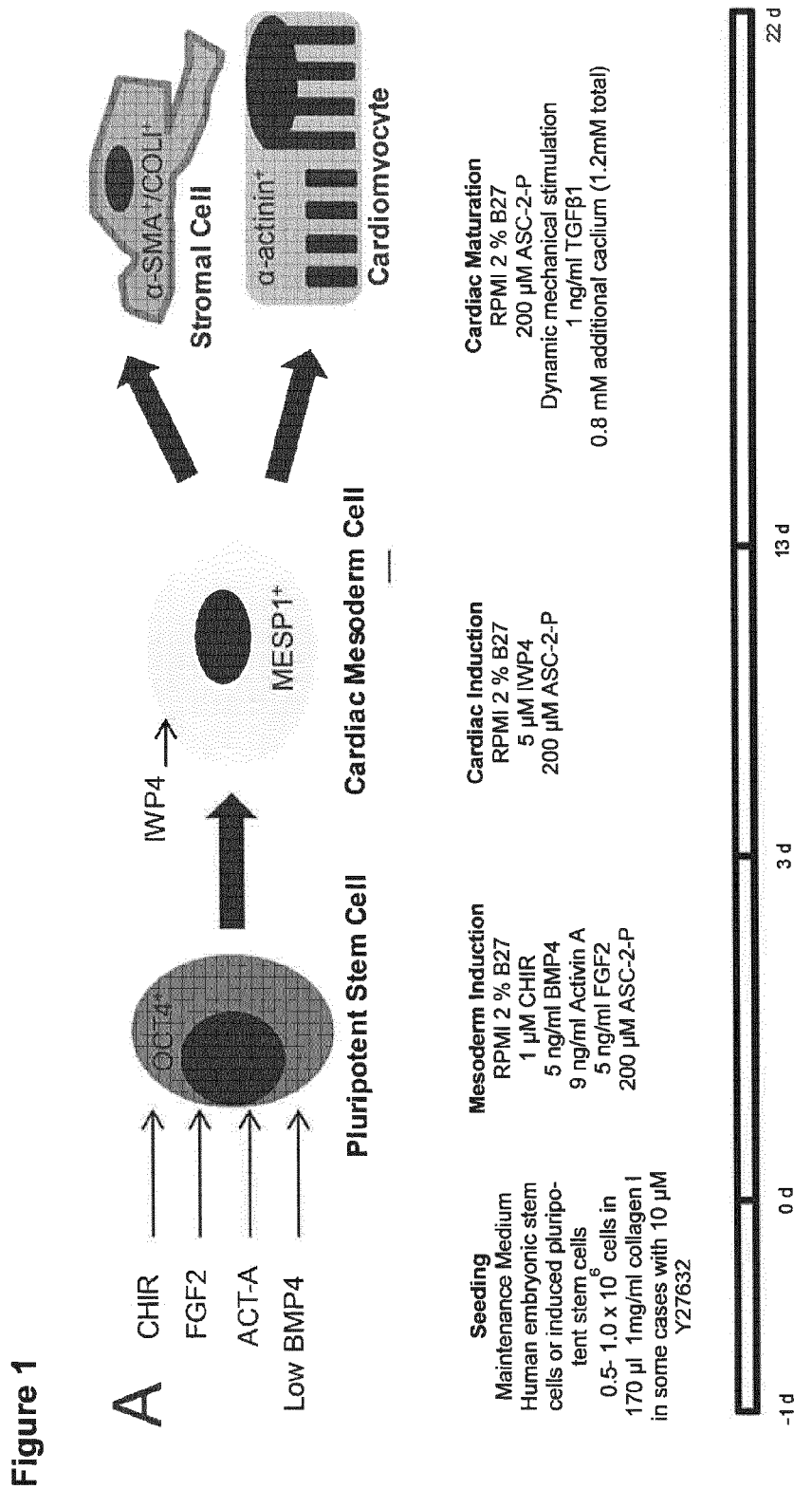
FIG. 1: Optimization of early cardiac differentiation for robust and efficient cardiac differentiation. (A) Schematic of the developed cardiac differentiation protocol. (B,C) Effect of FGF-2 addition on cardiac differentiation in 2D culture. (D,E) Effect of varying BMP4 concentration on cardiac differentiation in 2D culture whilst CHIR is present. (F,G) Effect of removing each factor individually from the 2D cardiac differentiation protocol, all factors were added daily from days 0-3 except IWP4 which was added every 2-3 days from days 3-13. (H,I,J) Assay for the presence of contaminating cell types using qPCR. (K) Immuno-staining for cardiomyocyte markers. (L) Flow cytometry for cardiomyocytes (n=6 experiments). (M) Immuno-staining for stromal cell markers. (N) Flow cytometry for stromal cells (n=6 experiments). All data is n=3 experiments unless otherwise noted. qPCR data (MESP-1, OCT4, SOX17 and NEU-ROD1) is normalized to GAPDH. * Indicates statistically significant difference (P<0.05) using ANOVA with Tukey's Multiple Comparison Post Hoc test.  Indicates statistically significant difference from samples supplemented with no factors. * Indicates statistically significant difference from samples supplemented with no factors, all factors minus BMP4, all factors minus ACT-A and all factors minus IWP-4.
Figure 1:
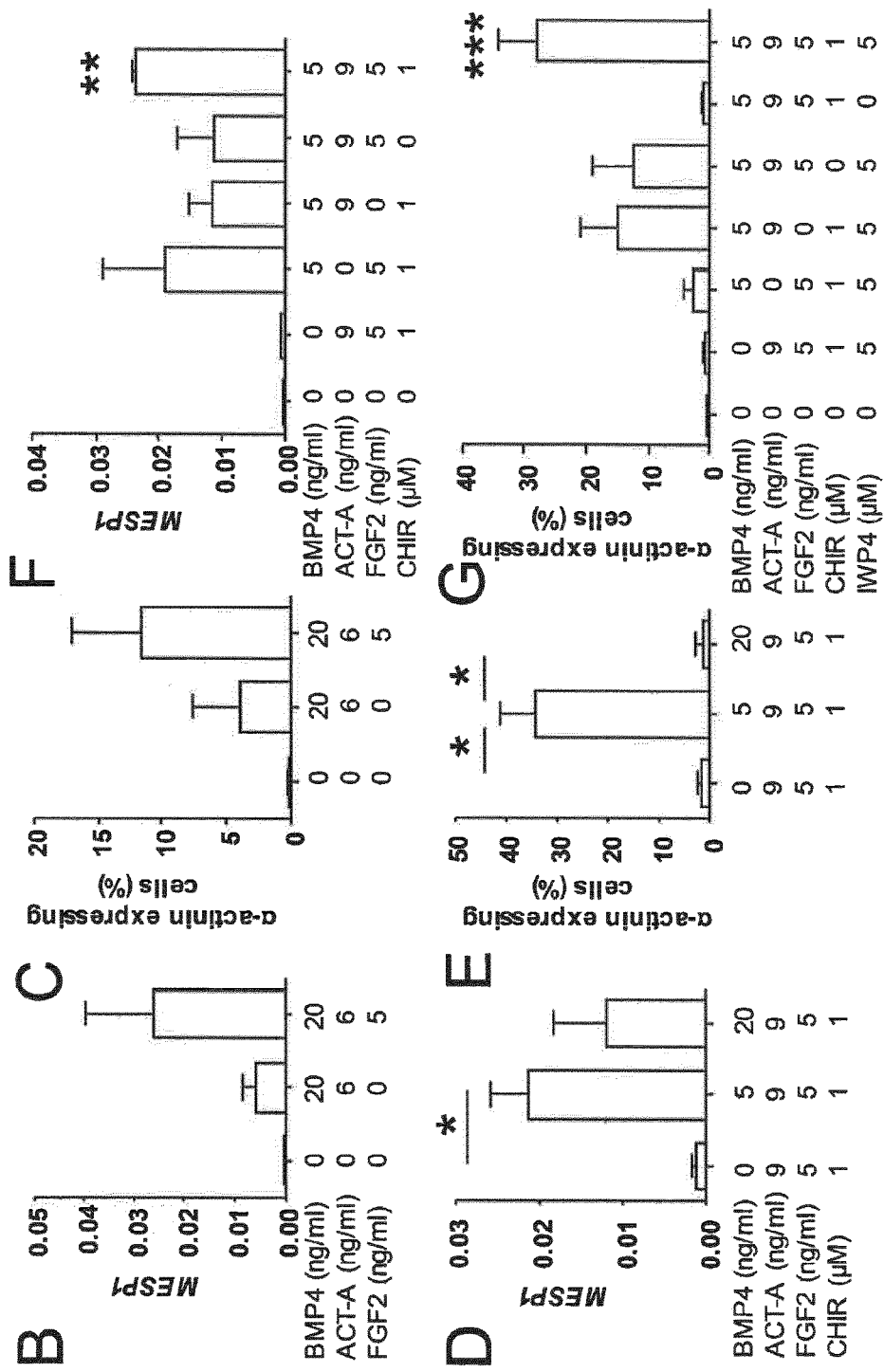
Figure 1:
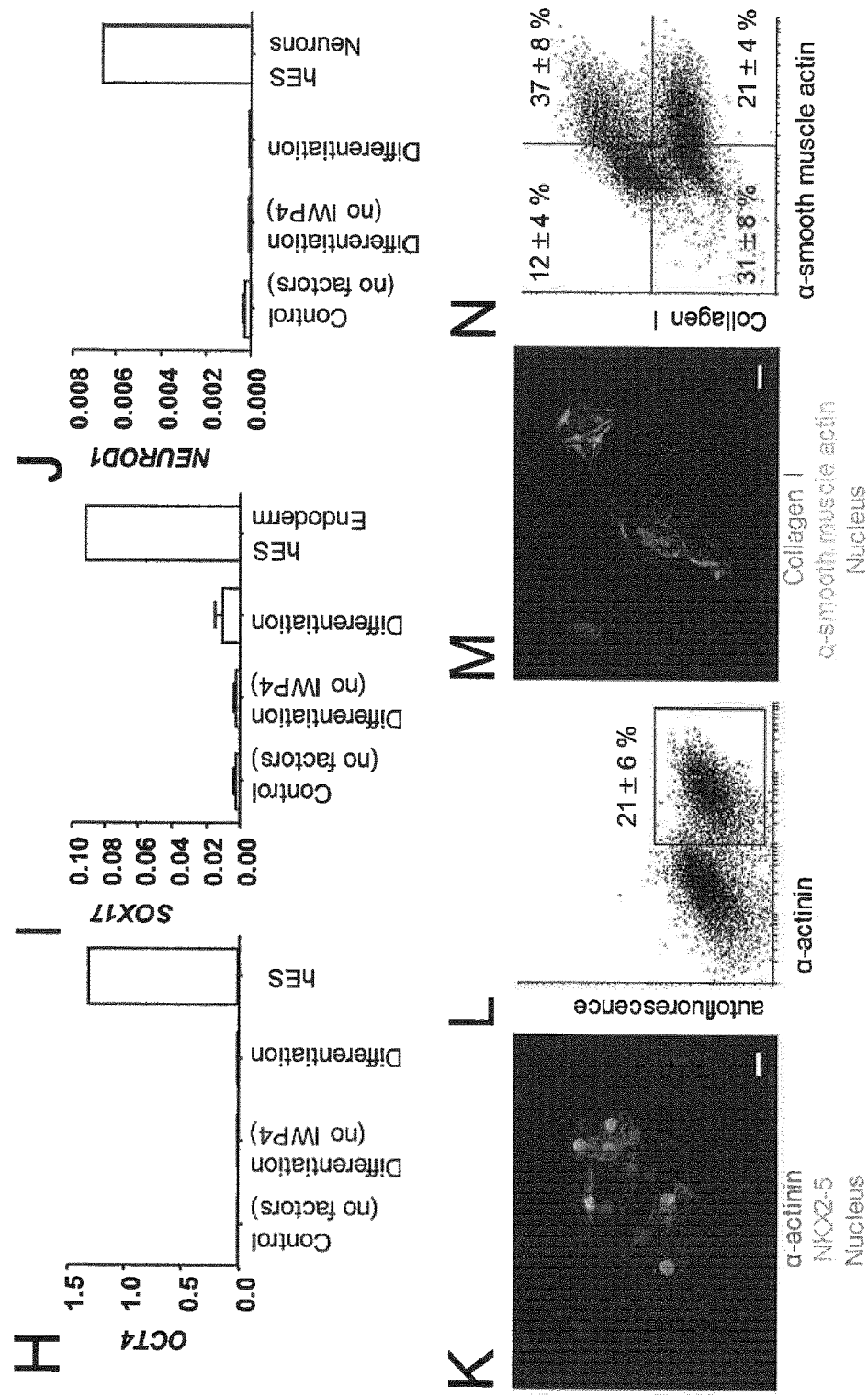

Cardiac Differentiation Requires Optimization of Early Cardiac Mesoderm Induction It has been demonstrated that non-myocyte cell fractions or stromal cells are essential for the function of engineered heart tissues. For this reason a cardiac differentiation protocol was firstly required which consistently produced cardiomyocytes and fibroblasts/stromal cells. The inventors optimized their cardiac differentiation protocol (FIG. 1a) for both yield and consistency, based on a previously published serum-free 2D hPSC differentiation protocol (Hudson et al. Stem Cells Dev 21, 1513-1523 (2012)). It was reasoned that robustness and efficiency could be enhanced if WNT activity was stabilized during the mesoderm induction phase. As surrogate marker for mesoderm induction MESP1 expression was analysed by qPCR on culture day 3; this was followed by flow cytometry for α-actinin (cardiomyocyte marker) at day 16, which were found correlated very well with the amount of beating activity. The most important steps for the progression from the previously published protocol to the new protocol are summarised in FIG. 1.

The earlier protocol used cardiac mesoderm induction with BMP4 and Activin-A for the first 3 days followed by cardiac specification using a WNT inhibitor IWP4 (Hudson et al Stem Cells Dev 21, 1513-1523 (2012)). Consistent with the essential requirement of FGF2 for early mesoderm formation in recent studies using hPSCs and in vivo development, the addition of 5 ng/ml FGF2 in during the first 3 days of differentiation resulted in a trend to increased MESP1 expression (FIG. 1b) and subsequently a trend to increased α-actinin (FIG. 1c). However, it was enforced WNT signalling that helped improve consistency and differentiation, consistent with its essential role in induction of early mesoderm. To enforce WNT signalling CHIR99021 was used, a small molecule inhibitor of GSK313 which induces WNT signalling even in the presence of canonical WNT inhibitors. CHIR alone or with the differentiation factors used in FIG. 1b,c was unable to induce any beating activity. When the BMP4 concentration was varied, optimal and consistent induction of MESP1 (FIG. 1d) and α-actinin expression (FIG. 1e) was found at a BMP4 concentration of 5 ng/ml. Each factor from the differentiation protocol was then individually removed to demonstrate its requirement in the efficient and consistent induction of MESP1 (FIG. 1f) and subsequently α-actinin expression (FIG. 1g).

In order to form BHM it is also important that stromal cell populations are present. It was therefore investigated whether stromal cells or other potentially contaminating cell types were present in the optimized differentiation protocol. Very low levels of potentially contaminating cell populations were found, analysed using qPCR for hPSCs (OCT4 also known as POU5F1) (FIG. 1h), endoderm (SOX17) (FIG. 1i), neural (NEUROD1) (FIG. 1j), and early mesoderm (MESP1) (data not shown). Very high expression of NKX2-5 and β-MHC (also known as MYH7) were found in the cardiac differentiation culture of the invention compared to the other conditions (with no factors or without IWP4, data not shown). Additionally it was found that both cardiomyocytes (FIG. 1k-l) and different stromal cell types, including: α-smooth muscle actin positive cells (α-SMA$^+$), collagen I positive cells (COLI$^+$) cells, and α-SMA$^+$COLI$^+$ cells were present (FIG. 1m,n). Together this data suggests that the cardiac differentiation protocol of the invention efficiently produces cardiomyocytes with the rest of the cells being predominantly stromal cells, thus providing the required cell composition for tissue engineering applications.

Directed Formation of BHM

After optimization of the cardiac differentiation protocol the hypothesis was tested whether one could form BHM directly from hPSCs. The new serum-free cardiac differentiation protocol (FIG. 1) was used with an additional maturation step where the rings were removed from the molds and put onto static stretchers (+10% of slack length) in medium containing 5 ng/ml FGF2 and 200 μM ascorbate-2-phosphate (ASC-2-P). It was found that this protocol was effective in forming BHM (FIG. 2a). The BHM started to contract spontaneously in different areas by day 13 and by day 15-17 the contractions became synchronous and rhythmic, and continued until analysis at day 22 (data not shown). The cardiomyocytes in the BHM had an elongated and striated morphology (FIG. 2b) and the BHM could be electrically paced and had a measurable force of contraction with responsiveness to calcium concentration (FIG. 2c).

Figure 5:
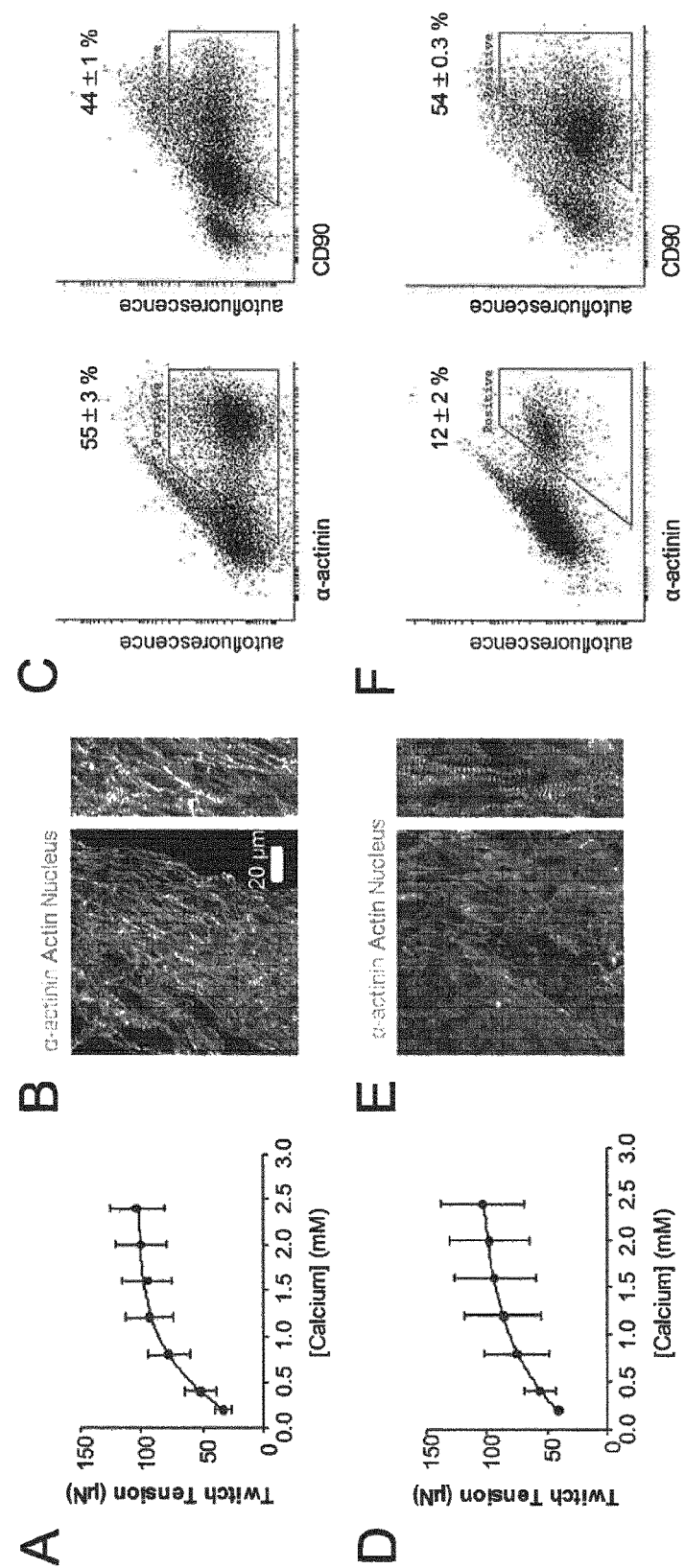
FIG. 5: The BHM protocol can be used in all tested PSC lines. (A,B,C) Data from HES3-BHM; (D,E,F) Data from hIPS-G1-BHM. (AD) Isometric twitch tension (force of contraction) in response to varying calcium concentration, n=4 for each line. (B,E) Whole-mount immuno-staining. (C,F) Flow cytometry analysis of cardimoycytes and stromal cells, n=3 per line.

The development of the BHM followed known developmental pathways. The hPSCs were largely differentiated by day 3 indicated by a decrease in TRA-1-60$^+$/OCT4$^+$ cells and OCT4 expression (FIG. 2d,f) and a concomitant expression of early mesodermal markers MIXL1 and MESP1 (FIG. 2f). By day 8 there was a loss of MIXL1 and MESP1 expression (FIG. 2f), with a concurrent increase in α-actinin$^+$ cells (FIG. 2d) and the expression of cardiomyocyte progenitor cell markers (FIG. 2f). There were peaks in the expression of multiple transcription factors involved in cardiogenesis, including: TBX5 (peak at day 13), ISL1 (peak at day 8), and NKX2-5 (peak at day 13) (FIG. 2f). This was followed by the expression of more mature cardiac markers α-MHC (also known as MYH6), fl-MHC, ANP (also known as NPPA), and MLC2v (also known as MYL2) (FIG. 2f). Interestingly, the expression of α-MHC peaked at day 13, followed by a large increase in β-MHC by day 22 and hence an increased β-MHC/α-MHC ratio (FIG. 2f). Furthermore, there was little expression of endodermal and neural markers at day 22 (FIG. 2f). Together this data suggests not only that the development of the BHM followed known developmental pathways, but also that cardiac maturation occurs as indicated by the drop in progenitor gene expression, increased β-MHC expression and β-MHC/α-MHC expression ratio, and increased expression of MLC2v (indicates maturity, see Tiburcy et al. Circ Res 109, 1105-1114 (2011)). Additionally, at day 22 it was found that the BHM was comprised of 30±6% (n=4 experiments) cardiomyocytes and a large proportion of stromal cells (FIG. 2d). Representative flow cytometry plots are shown in FIG. 5.

Optimization of BHM Functionality

Figure 2:
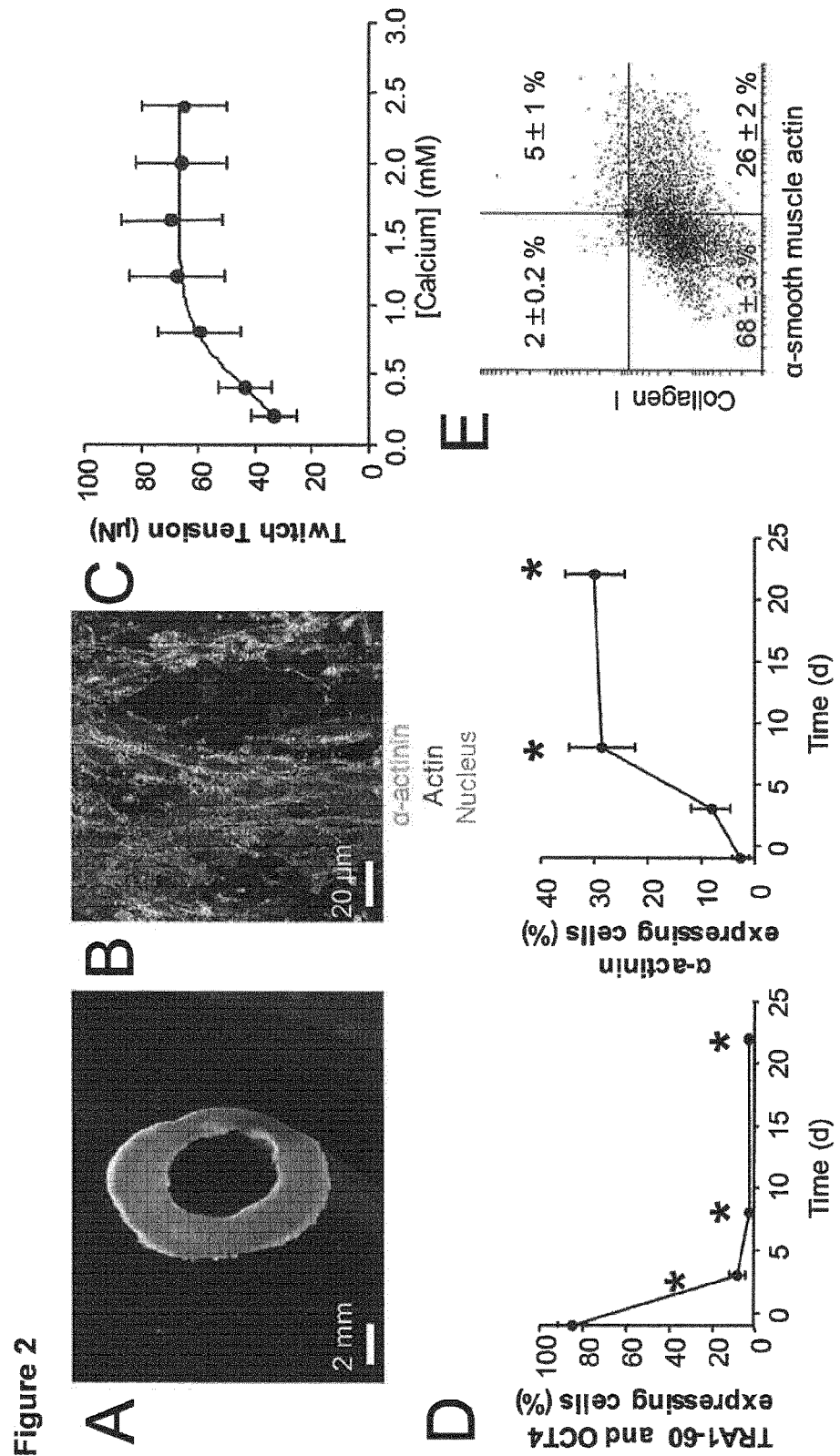
FIG. 2: BHM can be formed directly from hPSC. (A) BHM at 22 days of differentiation. (B) Whole-mount immunostaining. (C) Isometric twitch tension (force of contraction) in response to varying calcium concentration, n=7 from 4 experiments. (D) Flow cytometry profiles of pluripotency (TRA-1-60/OCT4) and cardiac markers (α-actinin), n=3-4 experiments. (E) Flow cytometry of stromal cell markers at day 22, n=3 experiments. (F) qPCR expression profiles of markers for pluripotency, mesodermal differentiation, and cardiac differentiation; data is normalized to GAPDH expression, n=3 experiments. * Indicates statistically significant difference (P<0.05) compared to −1 days using ANOVA with Tukey's Multiple Comparison Post Hoc test.
Figure 2:
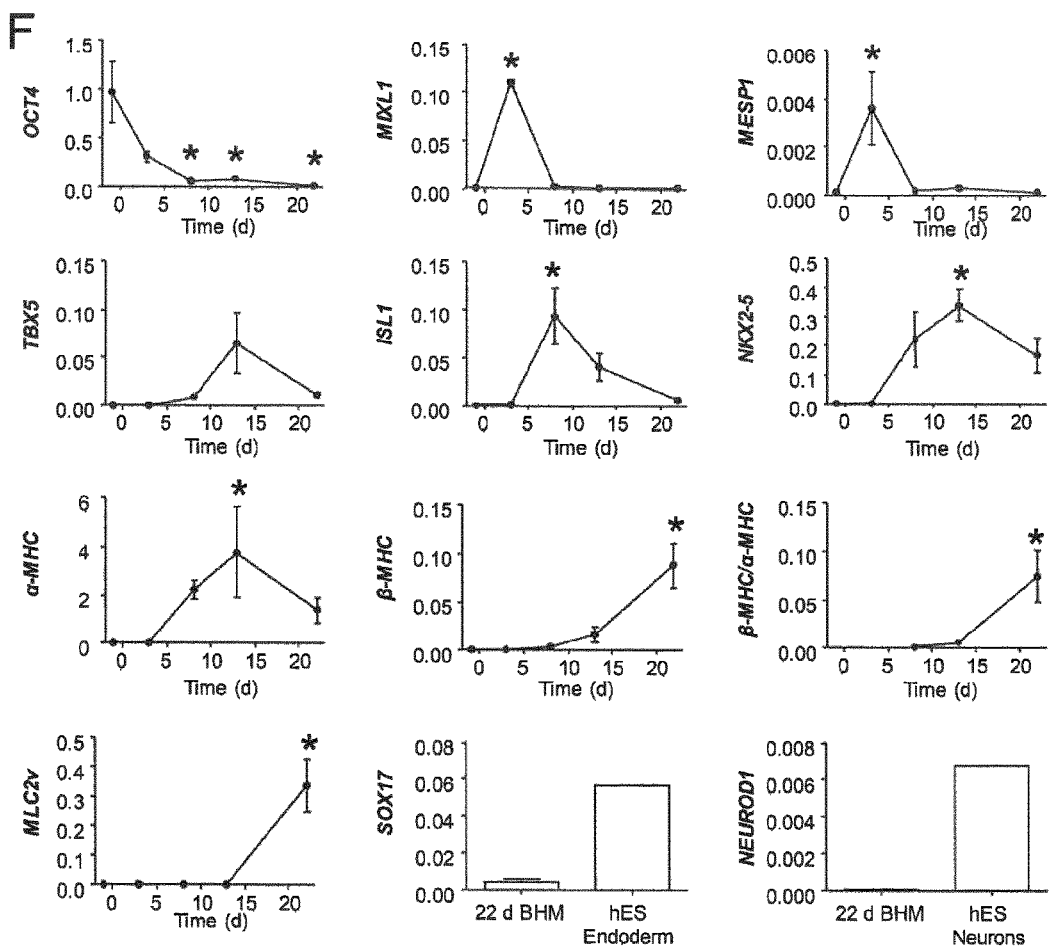
Figure 3:
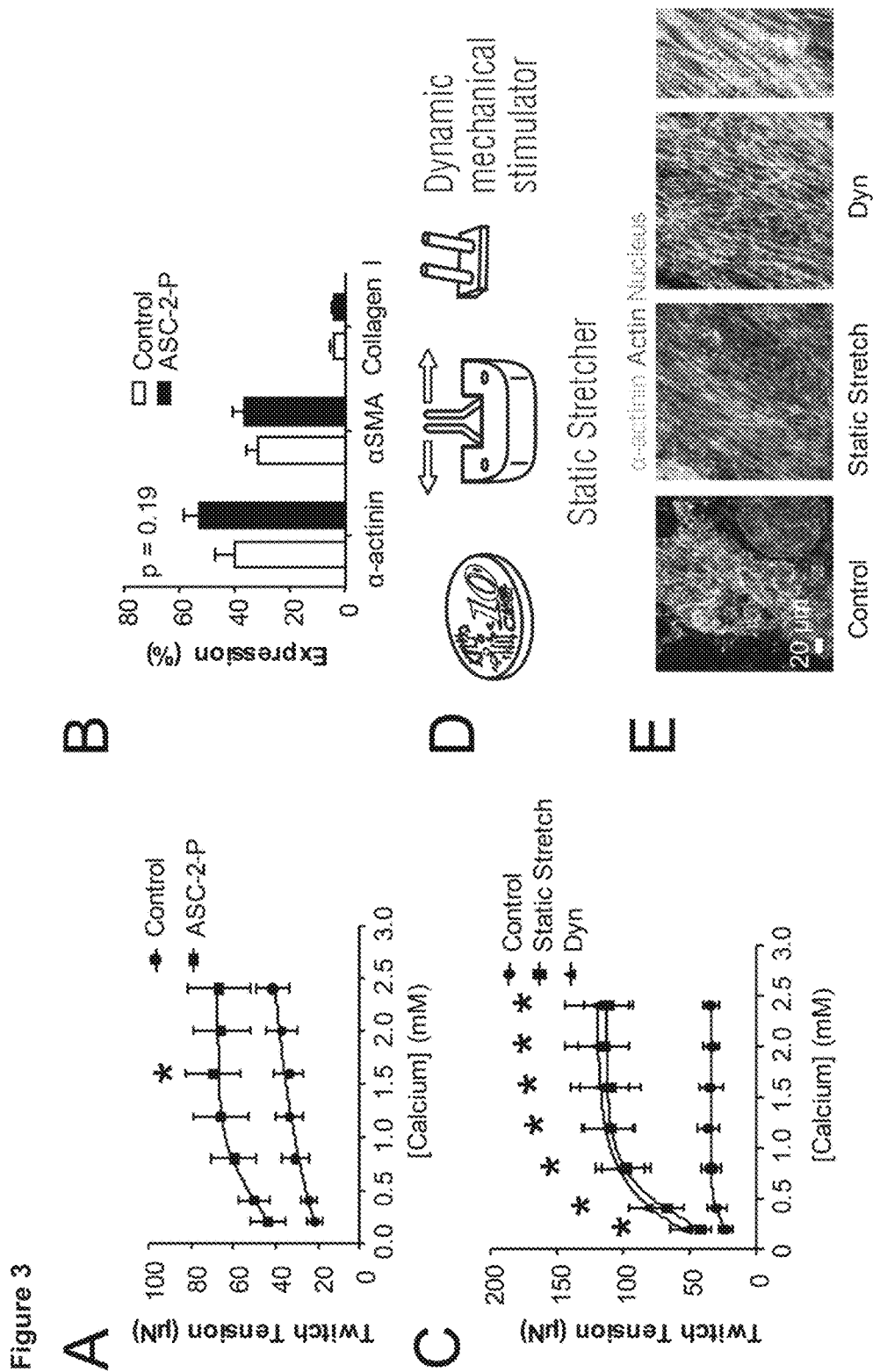
FIG. 3: Optimization of BHM culture condition reveals different parameters respond specifically to different stimuli. (A) ASC-2-P supplementation improves BHM, isometric twitch tension (force of contraction) in response to varying calcium concentration, n=8-9 from 3 experiments, * indicates statistically significant difference (P<0.05) compared to control using two-way ANOVA with Bonferroni post hoc tests. (B) Flow cytometry analysis of ASC-2-P experiments for cardiomyocyte and stromal cell markers, n=7-8 from 3 experiments. (C) Mechanical stimulation improves BHM function, isometric twitch tension (force of contraction) in response to varying calcium concentration, n=9-11 from 4 experiments, * indicates statistically significant difference (P<0.05) for both mechanical stimulation regimes compared to control using two-way ANOVA Bonferroni post hoc tests. (D) Mechanical stimulation devices. (E) Whole-mount immuno-staining of BHM under control and mechanical stimulation regimes. (F) Growth factors (FGF2:10 ng/mL and TGFb1:1 ng/mL) added during cardiac maturation regulate BHM function, isometric twitch tension (force of contraction) in response to varying calcium concentration, n=9-11 from 4 experiments. (G) Cardiomyocyte cell size analysis for the growth factor experiments using flow cytometry, n=6 from 3 experiments, * indicates statistically significant difference (P<0.05) compared to control using Student's t-test. (H) qPCR expression of β-MHC/α-MHC ratio for the growth factor experiments, n=3-6 experiments, * indicates statistically significant difference (P<0.05) compared to control using ANOVA with Tukey's Multiple Comparison Post Hoc test. (I) qPCR expression of ANP and Sk Act for the growth factor experiments, n=3 experiments. (J) Adjusting calcium to 1.2 mmol/L during cariac maturation improves BHM function, isometric twitch tension (force of contraction) in response to varying calcium concentration, n=10-11 from 4 experiments, * indicates statistically significant difference (P<0.05) compared to control using two-way ANOVA Bonferroni post hoc tests. (K) resting tension of BHM for the calcium experiments, n=10-11 from 4 experiments. (L) Elastic modulus of BHM for the calcium experiments, n=10-11 from 4 experiments, * indicates statistically significant difference (P<0.05) compared to control using ANOVA with Tukey's Multiple Comparison Post Hoc test.
Figure 3:
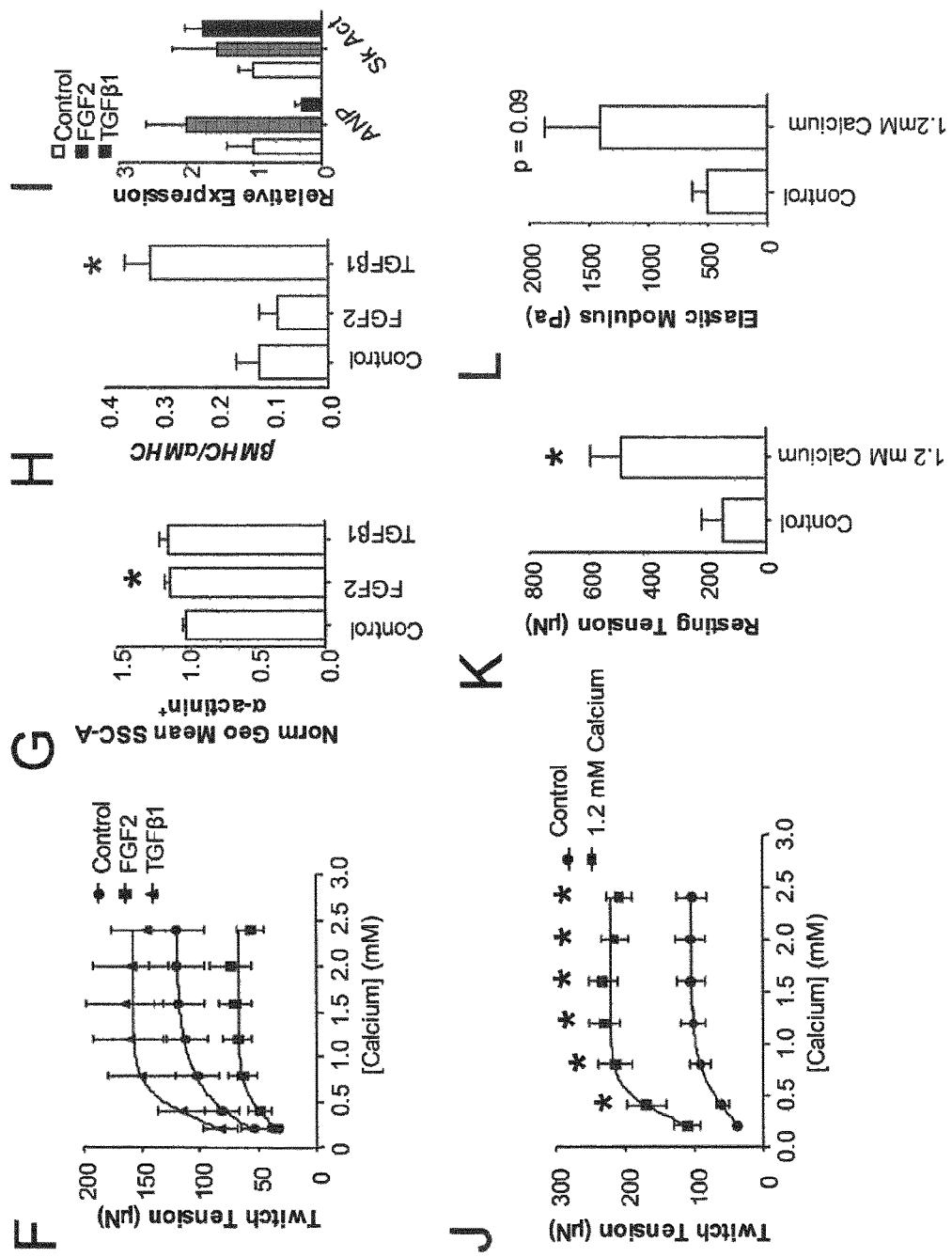

While the BHM protocol outlined in FIG. 2 represents the first entirely serum-free process of hPSC expansion and formation bioengineered myocardium, the inventors hypothesized that optimization could generate tissues with higher functionality and greater consistency. For these experiments contractile strength (twitch tension/force of contraction) was used as a primary determinant of function as twitch tension depends on a wide variety of myocardial properties including: cardiomyocyte number and phenotype, fibroblast number and phenotype, tissue connectivity, ECM composition, cell-cell connectivity and ECM-cell connectivity. As secondary factors the inventors used, 1) resting tension, because it reflects stroma cell function and extracellular matrix biology, 2) cardiomyocyte size, because of stimuli such as pharmacological stimuli, and 3) cell composition (cardiomyocytes:stroma cells), which is an important determinant for contractile performance. The parameters which changed are shown in FIG. 3.

ASC-2-P Enhances BHM Functionality

Ascorbate (vitamin C) plays a major role in the proper synthesis of collagen and is an antioxidant. It was therefore hypothesized that ascorbate (in the more stable form of ASC-2-P) supplemented during early BHM culture, days 0-13 (it was already added during days 13-22 in FIG. 2), would have a positive influence on BHM functionality given the importance of collagens during development. It was found that ASC-2-P significantly improved BHM twitch tension/force of contraction (FIG. 3a) and induced a trend to increased cardiomyocyte fraction with no change in the stromal cell fraction (FIG. 3b). It was also found that supplementation of ASC-2-P during the entire differentiation protocol improved differentiation in the inventor's 2D protocol by significantly increasing the number of cells without changes in cardiac differentiation efficiency (data not shown). Therefore, in both 2D and BHM formats, ASC-2-P may have increased cell survival and/or progenitor proliferation as proposed in a recent study (Cao et al. Cell Res 22, 219-236 (2012)).

BHM Function is Dependent on Mechanical Stimulation Regime

Next, it was assessed how static stretch and dynamic mechanical stimulation influenced BHM function. The devices used for static stretch and dynamic mechanical stimulation are shown in FIG. 3d. Both static stretch and dynamic mechanical stimulation significantly increased twitch tension/force of contraction of the BHM and both the mechanical stimulation regimes resulted in a similar BHM twitch tension (FIG. 3c). Both mechanical stimulation regimes improved the morphology of the cardiomyocytes in the BHM, causing compact, elongated and striated muscle bundles to form (FIG. 3d). Dynamic mechanical stimulation were preferred to static stretch, because it facilitates auxotonic contractions (Zimmermann et al, Nat Med 12, 452-458 (2006)).

Cardiomyocyte Properties are Dependant on Exogenous Growth Factors

There was a trend to decreased twitch tension/force of contraction when adding FGF2 and a trend to increased twitch tension when adding TGFβ1 (FIG. 3f). Therefore, in the previous experiments where FGF2 was added during cardiac maturation, this may have actually been detrimental BHM function. It was found that both FGF2 and TGFβ1 induced an increase in cardiomyocyte size (FIG. 3g). The addition of TGFβ1 resulted in a more mature β-MHC/α-MHC expression ratio (human heart=9) (FIG. 3h) while pathological hypertrophy markers ANP (also known as NPPA) was decreased (FIG. 3i). The addition of FGF2 did not change β-MHC/α-MHC expression ratio (FIG. 3h), but induced (variably) pathological hypertrophy marker ANP (FIG. 3i). Together this indicates both factors induce hypertrophy, which is consistent with in vivo results. However, FGF2 may be considered as an inducer of pathological hypertrophy, while TGFβ1 may be considered as an inducer of physiological hypertrophy.

In a further set of experiments the inventors investigated if supplementation of the culture medium with increasing TGFβ-1 during cardiac maturation phase has an influence in contractile function of BHM. The inventors observed an enhancement of contractile function of BHM in a concentration dependent manner (FIG. 10).

In the earlier experiments the inventors found a large reduction in α-smooth muscle actin and collagen I positive cells in the BHM when compared with the 2D protocol (FIG. 1n vs. FIG. 2e). This may be a reflection of subtle differences in myofibroblast/fibroblast differentiation in 2D and BHM cultures. To more homogeneously detect cardiac-fibroblast-like populations in hPSC-derived 2D and BHM cardiac differentiation cultures antibodies against the canonical CD90 (also known as THY1) were employed in subsequent experiments.

Adjusting Extracellular Calcium to Physiological Concentrations Improved BHM Function Calcium concentration is tightly regulated in human serum with physiological calcium concentrations of 2.25-2.75 mM and 1.0-1.2 mM, for total calcium and ionized calcium, respectively. Because the concentration of calcium in RPMI medium is quite low (0.42 mM) compared to physiological calcium it was therefore assessed whether adjustment of free calcium concentration improved both BHM maturation and functionality. Adjustment of calcium to 1.2 mM (using a 0.2 M $CaCl_2$ solution) greatly increased the twitch tension of the BHM (FIG. 3j). Moreover, an increase in resting tension (FIG. 3k) and elastic modulus (FIG. 3l) was observed. Optimal elastic modulus has been demonstrated to improve the mechanical work done by cardiomyocytes during contractions which may increase contraction force. The mechanism behind the increased elastic modulus in response to increased calcium is currently unknown. Importantly, it should be noted that there were no changes in calcium handling proteins that were assessed using qPCR (CASQ2, PLN, ATP2A2, and RYR2, data not shown, n=3 experiments).

Figure 4:
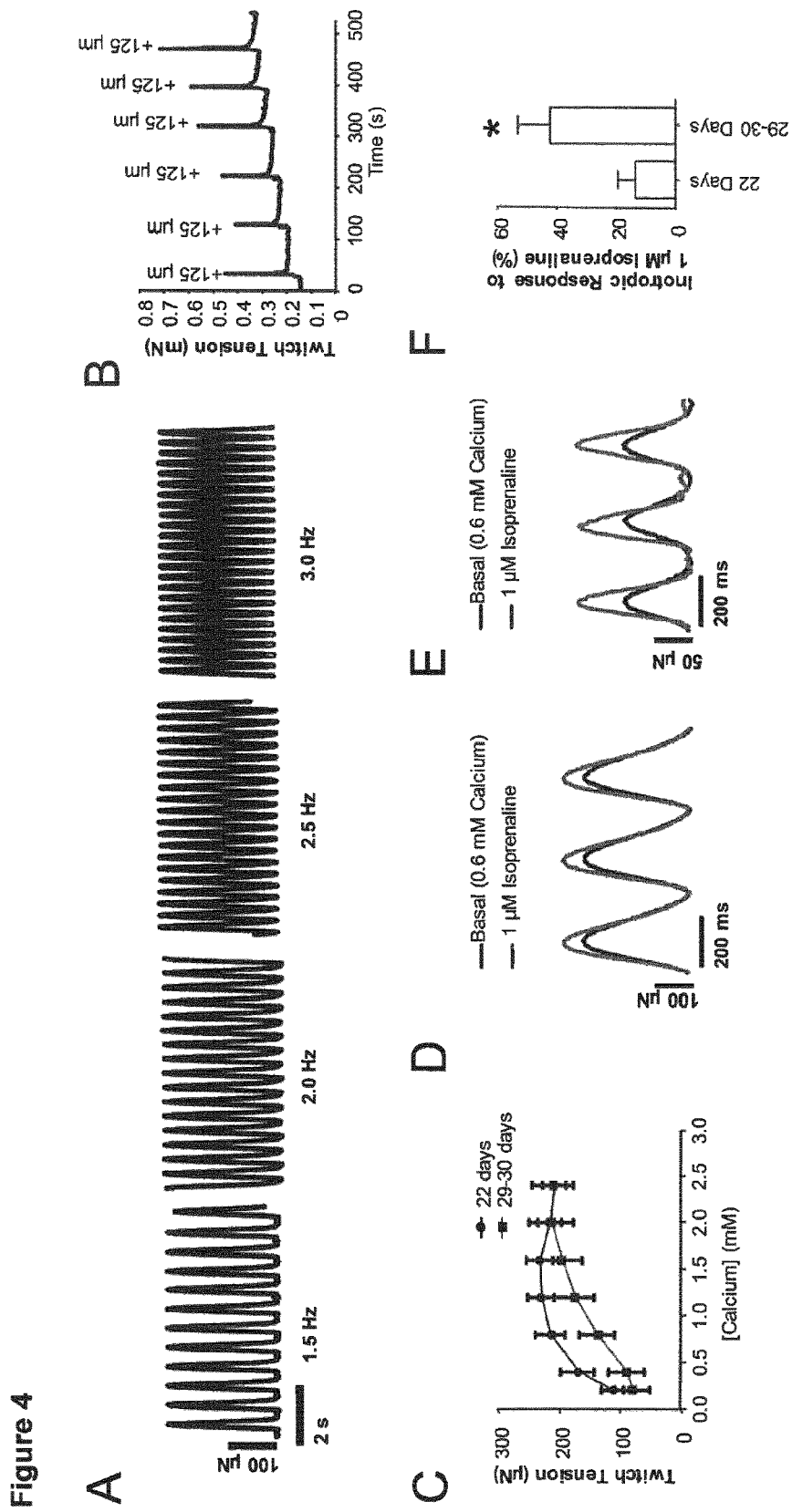
FIG. 4: BHM produced using the optimized protocol exhibit in-vivo-like properties. (A) BHM can be paced electrically at various rates. (B) BHM respond with increased twitch tension (force of contraction) to increased length (Frank-Starling mechanism). (C) Twitch tension (force of contraction) comparison of 22 day old (from previous data) and 29-30 day old BHM, n=11 from 4 experiments for 22 days and n=7 from 2 experiments for 29-30 days. (D) Inotropic response of 22 day old BHM to isoprenaline (1 μmol/L) under paced conditions at 0.6 mM calcium. (E) Inotropic response of 29-30 day old BHM to isoprenaline (1 μmol/L) under paced conditions at 0.6 mM calcium. (F) Comparison of inotropic response to isoprenaline (1 μmol/L) with age, n=11 from 4 experiments for 22 days and n=7 from 2 experiments for 29-30 days, * indicates statistically significant difference (p<0.05) using Student's t-test.

BHM Produced Using the Optimized Protocol Display In-Vivo Like Properties BHM contacted spontaneously and coherently, and could be paced electrically at multiple frequencies up to at least 3 Hz (FIG. 4a), covering the range of beating frequency observed during heart development. BHM also increased twitch tension (force of contraction) in response to increased resting length (and resting tension) consistent with the Frank-Starling mechanism (FIG. 4b). With increased culture time no change in BHM twitch tension compared to the previous data was found, but an increase in calcium $EC_{50}$ from 0.2 to 0.7 mmol/L was observed (FIG. 4c). Extended culture also resuited in an increased inotropic response to 1 µM isoprenaline indicating improved maturity over traditional culture formats where no increase has been observed (FIG. 4d-f). Using whole-mount immunostaining, it was found that the BHM also has both stromal cells and endothelial cells present in the muscle bundles (data not shown). Importantly BHM culture could also be maintained for long term (until at least day 63) under the maturation conditions with an observed improvement in morphological appearance (data not shown).

The Unmodified BHM Protocol Works on Multiple Human Pluripotent Stem Cell Lines

Figure 6:
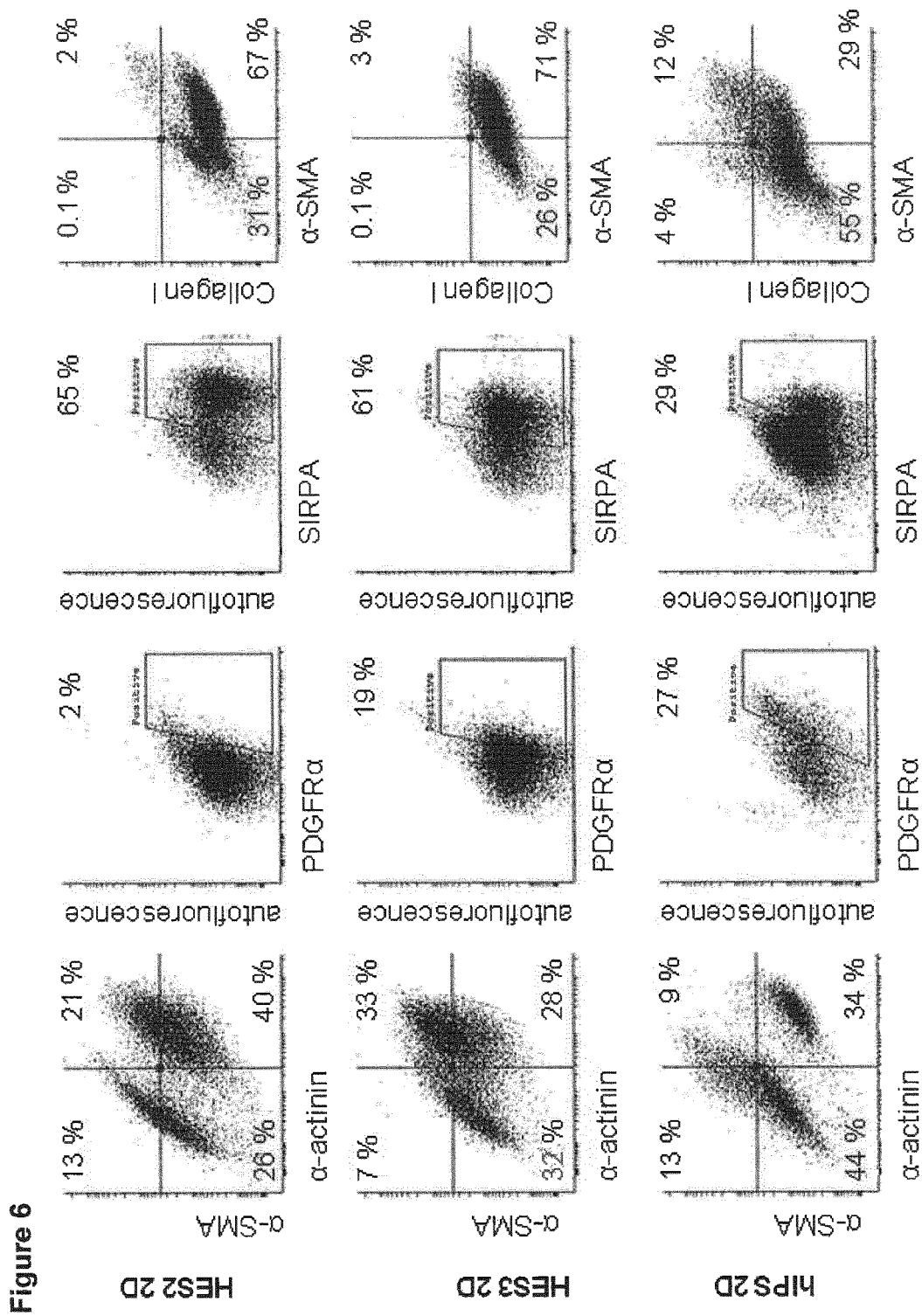
FIG. 6: 2D cardiac differentiation of multiple hPSC lines. Flow cytometry analysis of cardiac (α-actinin, SIRPA) and stromal cell markers (PDGFRα, α-SMA, collagen I).

Next, it was demonstrated that the optimized BHM (FIGS. 5) and 2D (FIG. 6) protocols work on multiple hPSC lines. For these analyses HES2, HES3 and hIPS-G1 lines (reprogrammed dental fibroblasts using vector-free Cytotune reprogramming kit) were used. It is important to note that for both the 2D and BHM protocols it was found that modification of the seeding cell number or the use of a Rho-associated protein kinase inhibitor (10 μM, Y-27632) was required to achieve similar cell densities in all lines after the initial 24 h seeding phase (data not shown). When using the required seeding protocol for a particular cell line the 2D and BHM protocols could be used un-modified for those lines.

It was found that both the HES3 line and the hIPS line produced BHM with a lower twitch tension (FIG. 5a,d) compared to the HES2 line (FIG. 3j). However, both the HES3 and hIPS BHM had similar morphologies (FIG. 5b,e). The cardiomyocyte fractions for the HES3 BHM was similar (FIG. 5c) and for the hIPS BHM was lower (FIG. 5f), compared to the HES2 BHM. The decreased functionality in the BHM from these lines is most likely from a lower cell number in the HES3 BHM ($0.50\pm0.03\times10^6$ cells, n=3) and hIPS BHM ($0.55\pm0.05\times10^6$ cells, n=3), compared to the HES2 BHM ($0.74\pm0.13\times10^6$ cells, n=6 from 3 experiments). Therefore, care must be taken to exclude differences caused by changes in cell number and composition when assessing different cell lines rather than different treatments on the same line.

BHM as a Developmental Model Reveals that BMP Signalling is Required for Terminal Differentiation of Human Cardiomyocytes Inhibition of BMP signalling is embryonically lethal even when effects are restricted (or at least partially restricted) to the developing heart using CRE driven by various genes (for a review please see Kruithof et al. Differentiation 84, 89-102 (2012)). In these studies there have been multiple processes ascribed to BMP signalling including structural defects, myocardial properties including trabeculae structure and wall thickness, and cell phenotype including dysregulation of progenitor genes and reduced epithelial-to-mesenchymal transformation (EMT). In order to determine the effect of BMP signalling purely on myocardial development without systemic influences and anatomical limitations, BHM was therefore deemed to be a good model system.

Figure 7:
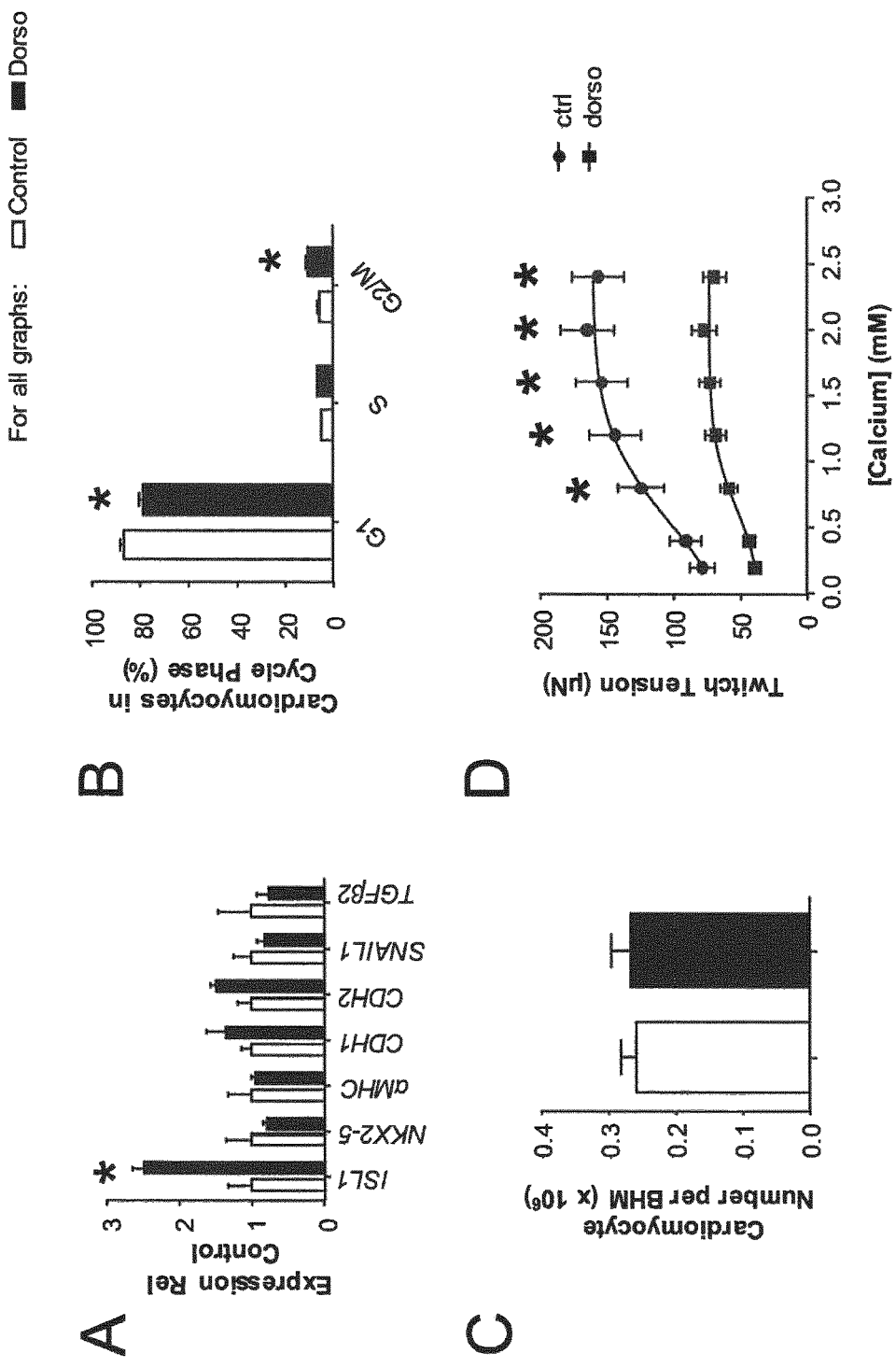
FIG. 7: The BHM can be used to model developmental processes, using BMP signalling inhibition as an example. (A) qPCR analysis of multiple markers at day 13 of BHM formation. (B) Cell cycle analysis using flow cytometry gating on α-actinin+ cells. (C) Cardiomyocyte number per BHM. (D) Isometric twitch tension (force of contraction) in response to varying calcium concentrations. * indicates statistically significant difference (P<0.05) compared to control using A+B) Student's t-test (n=3-4) or D) two-way ANOVA Sidak's Multiple Comparison post test.

In these experiments 2 μmol/L of the BMP receptor signalling inhibitor dorsomorphin were added with each medium exchange from day 6 onwards. At day 13 the dorsomorphin treated BHM failed to down regulate ISL1 while the expression of other more mature cardiac markers NKX2-5 and α-MHC were not altered (FIG. 7a). When investigating EMT associated genes, it was found that there was no alteration in CDH1, CHD2, SNAIL1 or TGFβ2 expression indicating that EMT or factors regulating EMT were not altered in BHM after 13 days (FIG. 7a). Using flow cytometry after 22 days it was found that there were more cardiomyocytes in the active cell cycle in the dorsomorphin treated group (FIG. 7b). However, it was found that treatment with dorsomorphin did not alter the cardiomyocyte number (FIG. 7c). It was also found that the total cell number per BHM and the fractions of cardiomyocytes (α-actinin$^+$) and stromal cells (CD90$^+$) did not change in the dorsomorphin treated group (data not shown). Despite these similarities there was a large reduction in twitch tension/force of contraction to 47% of the control group in the dorsomorphin treated BHM (FIG. 7d). Interestingly, there was neither a change in BHM responsiveness to isoprenaline nor a change in cardiomyocyte size in the dorsomorphin treated BHM (data not shown).

As increased cell cycle activity did not lead to increased cardiomyocyte number and reduced twitch tension, it was calculated whether oxygen concentration may limit cardiomyocyte number in the BHM. To determine if this was the case, mathematically modelled oxygen diffusion profiles were based on models reported in the literature and the parameters in the different BHM conditions (cell number, cardiomyocyte fraction and size). It was found that when using the parameters for the control BHM there was no hypoxic region, even if the number of cardiomyocytes increased to 125% (data not shown).

Together the present data suggests that BMP inhibition using dorsomorphin results in an increased proliferative state, a result which is consistent with mouse in vivo experiments. However, there was no increase in cardiomyocyte number indicating that either there is increased apoptosis or the cardioymocytes are bi-nucleating. Regardless of the mechanism, inhibition of BMP signalling resulted reproducibly in a tissue phenotype that produces less contractile force (and also lower force per cardiomyocyte) and inferior myocardial tissue.

Custom-Made Supplement to Replace B27®

BHMs were generated from undifferentiated hESC under serum-free conditions according to standard BHM protocol. The standard protocol includes B27® supplement. In this experiment B27® supplement was replaced by a defined, custom-made supplement (CMS, Table 4).

Figure 9:
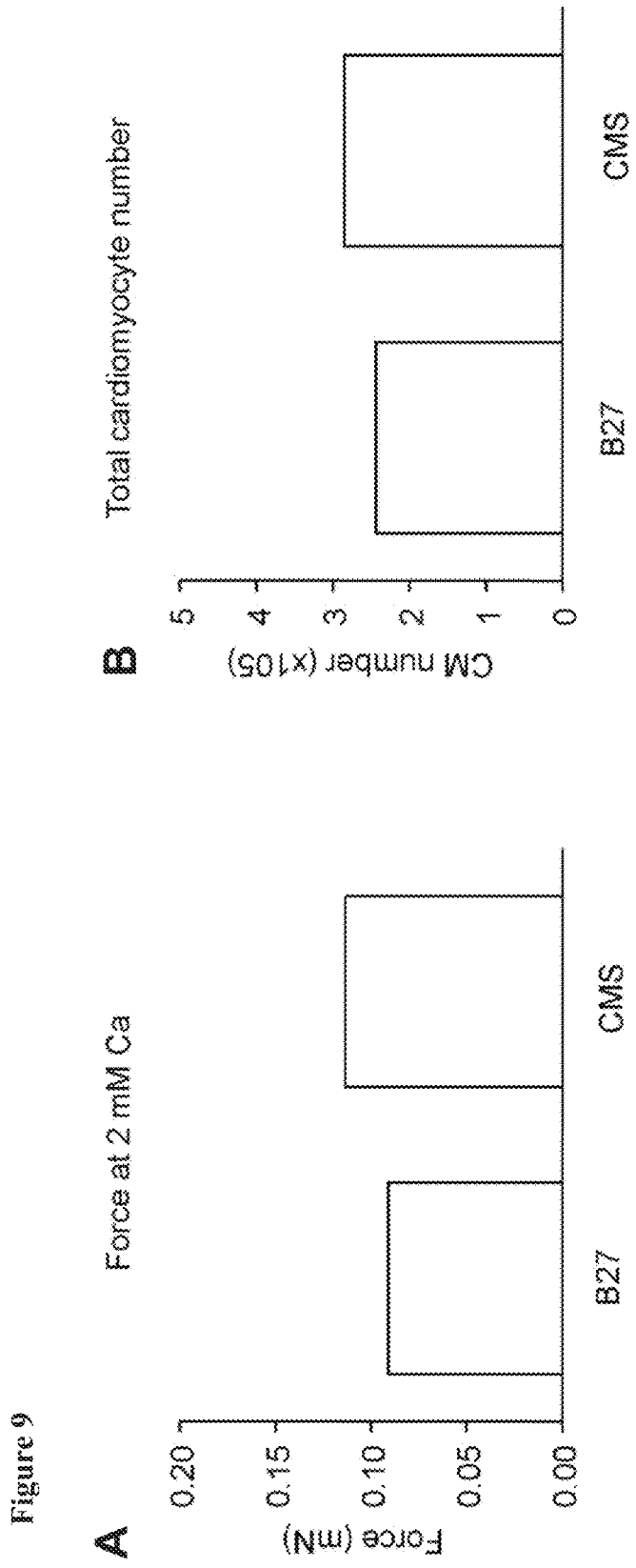
FIG. 9: Custom-made supplement to replace B27®. (A) Contractile force of BHMs (hES2) made with B27® or custom-made supplement (CMS) at 2 mM extracellular calcium, n=2/group. (B) Total CM number in BHM made with B27® or custom-made supplement (CMS), n=2/group.

The results show that B27® can be replaced by CMS. The force is similar, also the number of cardiomyocytes generated within the BHM is comparable (FIG. 9).

CONCLUSION

Using directed differentiation of PSCs in collagen I hydrogels the present application demonstrates that it is possible to guide BHM assembly under serum-free conditions. BHM has multiple applications including pharmacological studies, study of developmental processes, heart maturation processes and also potential regenerative applications.

In these examples, the robustness of the newly developed protocol was demonstrated by using multiple culture formats and multiple lines for differentiation. It will however be noted that while the experiment-experiment differentiation efficiency was consistent, the efficiency did vary when different batches of reagents were used. It is therefore prudent to establish strict reagent quality control in order to produce BHM with consistent and defined properties for both in vitro and potential therapeutic applications.

Methods

PSC Culture

HES2-ROSA26-RFP (Irion et al. Nat Biotechnol 25, 1477-1482 (2007)) cells were obtained from Gordon Keller and HES3 cells were obtained from Embryonic Stem Cell International (ESI, Singapore). hIPS were generated from human gingiva biopsy-derived fibroblasts using the Cytotune Reprogramming Kit (Applied Biosystems) following the manufacturer's instructions.

For IPS generation, 6 days after viral transduction fibroblasts were plated on irradiated mouse embryonic fibroblasts in fibroblast medium (DMEM high glucose, 2 mmol/L glutamine, 10% FBS (PM), 100 IU/ml Penicillin, 100 µg/ml Streptomycin, all Gibco except where indicated). The next day the medium was exchanged to PSC-medium (Knock-out DMEM (Gibco) supplemented with 20% Knock-Out Serum Replacement (KSR, Gibco), 2 mmol/L glutamine, 100 IU/ml Penicillin, 100 µg/ml Streptomycin, 1% non-essential amino acids (Gibco), and 10 ng/mL FGF2 (Miltenyi Biotec)). Emerging iPS colonies were mechanically picked and expanded by weekly passaging using 1 mg/ml Collagenase NB6 (Cresent Chemical Company).

For experiments, hPSCs were single cell adapted and cultured on irradiated human foreskin fibroblasts (HFF) in PSC-medium with daily medium changes and weekly passaging using 3 min TrypLE (Gibco) treatment (Ellerstrom et al., Stem Cells 25, 1690-1696 (2007)). Before characterization or differentiation experiments, the hPSCs were plated on 1:30 Matrigel (Millipore) in PBS (Gibco) coated-plates, at $2.5 \times 10^4$ cells/cm$^2$ for HES2 or $5 \times 10^4$ cells/cm$^2$ for HES3 and hIPS lines, and cultured for 3 days in 1:1 PSC-medium minus FGF-2 and HFF-conditioned medium (HFF-CM—harvested from 5 day confluent irradiated HFF cultures) with 10 ng/mL FGF2. The hIPS line also received 10 µmol/L Y-27632 (Stemgent). hPSCs were harvested for experiments by passaging using 3 min TrypLE treatment and then cultured in the appropriate format.

Pluripotent stem cell lines were regularly tested for *mycoplasma* using a test kit (Lonza) and characterized using standard assays. Pluripotency markers were assessed via PCR (endogenous OCT4, SOX2, KLF4, MYC), qPCR (OCT4, NANOG, REX1, DNMT3B) and immunostaining (OCT4, NANOG, TRA-1-60) (Chan et al. Nat Biotechnol 27, 1033-1037 (2009)). Demethylation of the OCT4 promoter was confirmed via bisulfite sequencing (Freberg et al. Mol Biol Cell 18, 1543-1553 (2007)). Karyotyping was used to determine if there were any genetic abnormalities (Campos et al. 3 Vis Exp 4 (2009)). Pluripotency was confirmed via teratoma formation in SCID mice via flank injection of $4$-$6 \times 10^6$ cells.

Differentiation Medium

For differentiation experiments the hPSCs were then cultured in RPMI 1640 supplemented with 1 mmol/L sodium pyruvate, 100 IU Penicillin, 100 µg/ml Streptomycin and 2% B27 supplement (SF medium, all Gibco) and various factors as indicated. Factors used in this study included: L-ascorbic acid 2 phosphate sesquimagnesium salt hydrate (Sigma), BMP4 (R&D Systems), Activin A (R&D Systems), FGF2 (Miltenyi Biotec), dorsomorphin (Stemgent), CHIR99021 (Stemgent), IWP4 (Stemgent), and TGFβ1 (Peprotech).

2D Cardiac Differentiation

Figure 8:
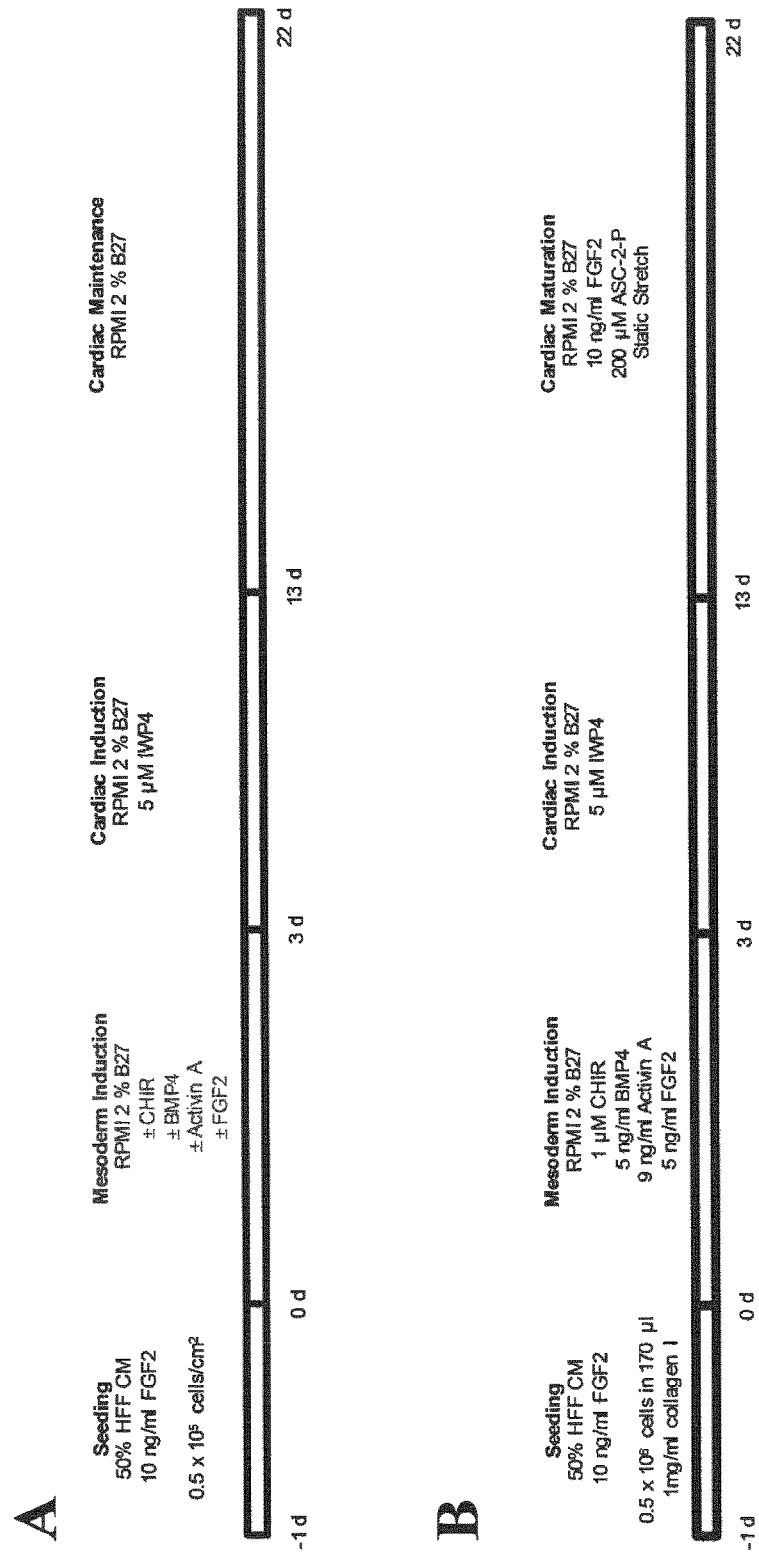
FIG. 8: Summary of protocols used for 2D cardiac differentiation and BHM formation. (A) Protocol used for experiments shown in FIG. 1. (B) Protocol used for experiments shown in FIG. 2. (C) Protocol used for experiments shown in FIG. 3—addition of ascorbic acid. (D) Protocol used for experiments shown in FIG. 3—mechanical stimulation and growth factors. (E) Protocol used for experiments shown in FIG. 3—addition of calcium. (F) Protocol used for experiments shown in FIG. 5. (G) Protocol used for experiments shown in FIG. 6. (H) Protocol used for experiments shown in FIG. 7.
Figure 8:
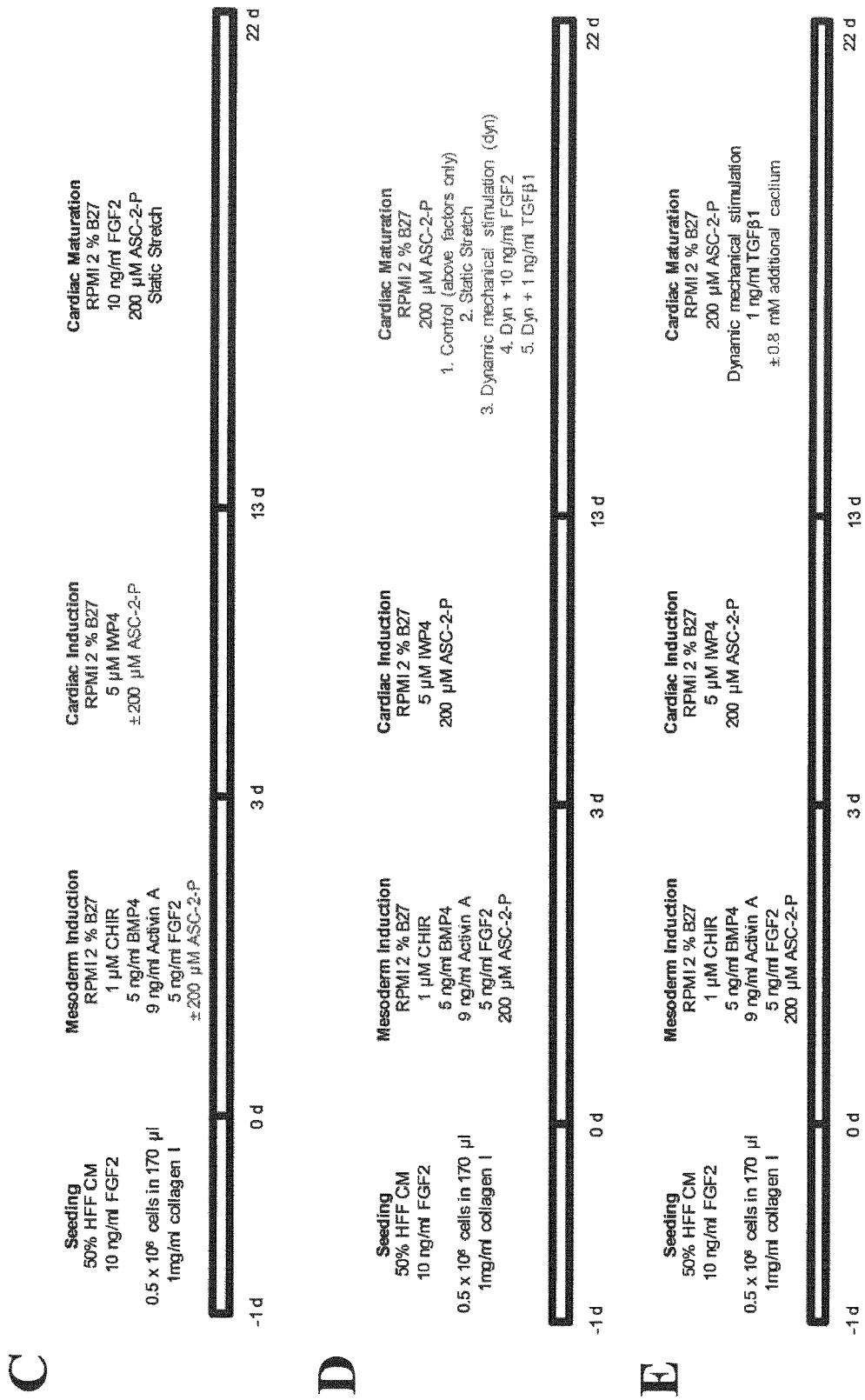
Figure 8:
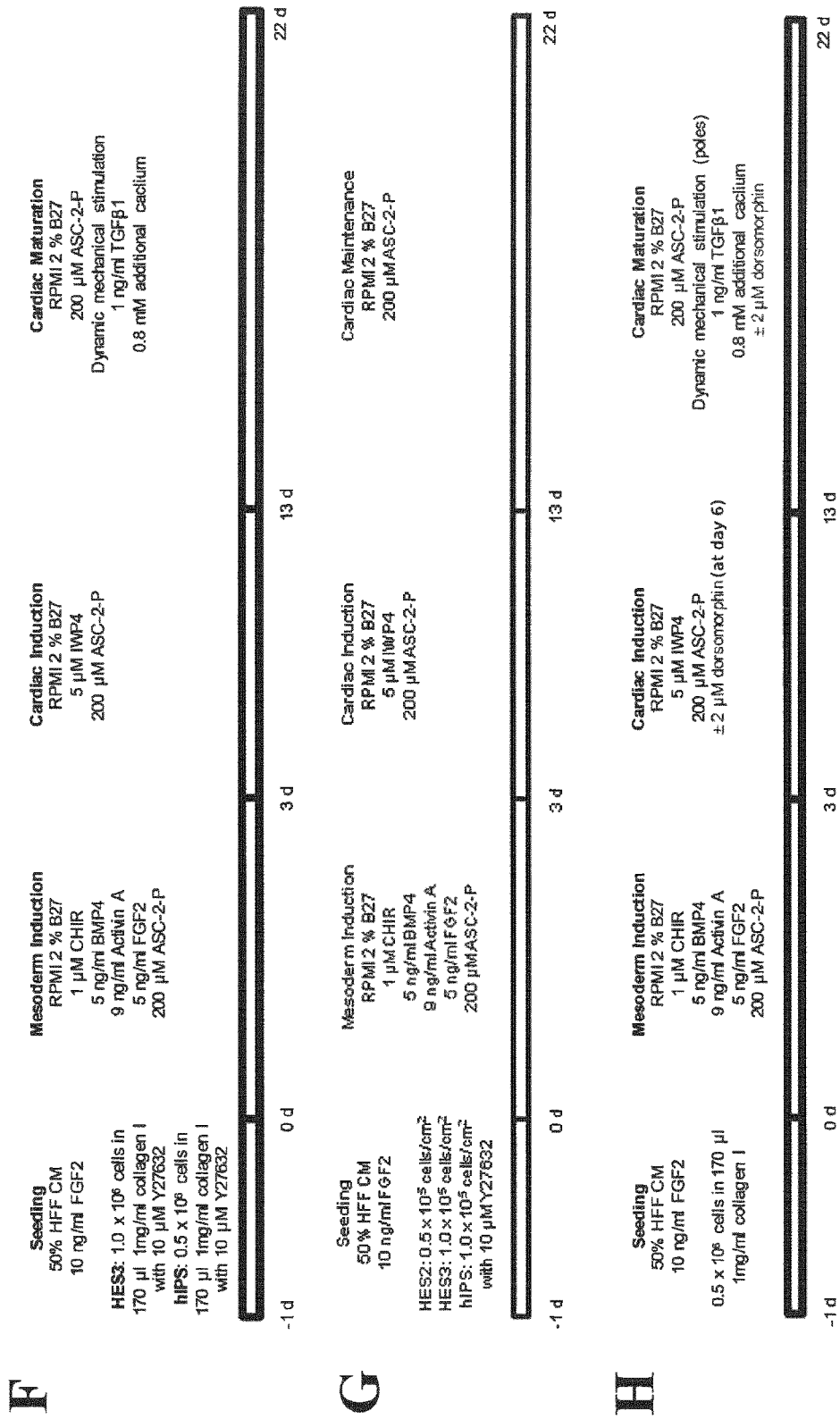

Cardiac differentiation was optimized on the HES2 line. HES2 hPSCs were plated at $5 \times 10^4$ cells/cm$^2$ ($1 \times 10^5$ cells/cm$^2$ for HES3 and hIPS lines) on 1:30 Matrigel/PBS coated-plates and cultured in 1:1 PSC-medium minus FGF-2 and HFF-conditioned medium (HFF-CM—harvested from 5 day confluent irradiated HFF cultures) with 10 ng/mL FGF2. For the hIPS line 10 µM Y-27632 was added to this medium. After 1 day the cells were rinsed with RPMI medium, then differentiated as indicated in each figure with 0.5 ml of medium in each well of a 24 well plate. The protocol details for each figure are outlined in FIG. 8.

BHM Formation

BHM formation was optimized on the HES2 line. HES2 hPSCs were suspended 1:1 in PSC-medium minus FGF-2 and HFF-conditioned medium (HFF-CM—harvested from 5 day confluent irradiated HFF cultures) with 10 ng/mL FGF2 and mixed with a collagen I hydrogel. For the HES3, and hIPS lines 10 µM Y-27632 was also added to the medium. The collagen I matrix was formulated with acid-soluabilized bovine collagen I (Devro) with an equi-volume of 2×DMEM (Gibco) and neutralized using 0.1 M sodium hydroxide. The hPSC/collagen I matrix was formulated to give a final collagen I concentration of 1 mg/ml and $5 \times 10^5$ hPSC per 170 µl. For the HES3 and hIPS lines $1 \times 10^6$ and $0.5 \times 10^6$ cells were used respectively per 170 µl. For each BHM, 170 µl of the hPSC/collagen I matrix was pipette into circular molds (i.d.=4 mm, o.d.=10 mm) fabricated using poly(dimethylsiloxane) (Sylgard, Dow Corning). After 10 min of culture in the incubator at 37° C. the collagen gelled and 1.25 ml of 1:1 human foreskin fibroblast-conditioned medium with 10 ng/ml FGF2 was added per BHM. The following day the BHMs were rinsed with RPMI medium and then differentiated as indicated in each figure, with 1.25 ml of medium per BHM. At day 13 the BHM were transferred onto mechanical stimulators as indicated. The protocol details for each figure are outlined in FIG. 8.

Cell Disassociation 2D cultures were disassociated by rinsing with PBS followed by incubation for 1 h in 1 mg/ml collagenase type I (Sigma) with 20% fetal bovine serum (FBS, Applied Biosystems) in PBS. The cells were then collected in a tube, rinsed with PBS and incubated with 0.25% Trypsin-EDTA (Applied Biosystems) for 5 min followed by rinsing with FBS containing medium.

For the initial BHM digestion protocol, BHMs were disassociated in 0.025 mg/ml Liberase TM (Roche), 30 mM 2,3-butanedione monoxime at 37° C. for 60 min in PBS. To preserve cell surface markers, BHM was disassociated using the same protocol as for the 2D digestion.

Quantitative PCR (qPCR)

Cells, BHMs or human heart biopsies were harvested and stored at −80° C. until RNA extraction using Trizol following manufacturer's instructions (Applied Biosystems). 1 µg of RNA was then treated with DNAse (Roche) followed by cDNA synthesis using a High Capacity cDNA Reverse Transcription Kit (Applied Biosystems). qPCR was performed using Fast SYBR Green Master Mix (Applied Biosystems) on a 384-well format AB7900 HT (Applied Biosystems). Gene expression was normalized using $2^{-\Delta Ct}$ or $2^{-\Delta\Delta Ct}$ using GAPDH as the housekeeping gene which we found to be consistently expressed between conditions in all of our experiments. Primer details are given in below Table 1.

TABLE 1

| Gene (Acc #) | F | R | Purpose | Size (bp) |
|---|---|---|---|---|
| GAPDH (NM_002046.3) | CCTCAAGATCATCAGCAATGCC (SEQ ID NO: 1) | ATGTTCTGGAGAGCCCCGC (SEQ ID NO: 2) | qPCR RT-PCR | 189 |

TABLE 1-continued

| Gene (Acc #) | F | R | Purpose | Size (bp) |
|---|---|---|---|---|
| OCT4 (NM_002701, NM_203289, NM_001173531) | CAGTGCCCGAAACCC ACAC (SEQ ID NO: 3) | GGAGACCCAGCAGCC TCAAA (SEQ ID NO: 4) | qPCR | 161 |
| NANOG (NM_024865) | CAGAAGGCCTCAGCA CCTAC (SEQ ID NO: 5) | ATTGTTCCAGGTCTG GTTGC (SEQ ID NO: 6) | qPCR | 111 |
| REX1 (NM_174900.3) | CACCGCCTCCCTTGG GAATTCAG (SEQ ID NO: 7) | TGTTCTGTTCACACA GGCTCCAGC (SEQ ID NO: 8) | qPCR | 83 |
| DNMT3B (NM_175848.1 NM_175849.1 NM_006892.3) | GGCCCAAGTAAACCT AGCTCGGC (SEQ ID NO: 9) | ATGCCTGGTGTCTCC CTTCATGC (SEQ IOD NO: 10) | qPCR | 168 |
| MIXL1 (NM_031944) | CCGAGTCCAGGATCC AGGTA (SEQ ID NO: 11) | CTCTGACGCCGAGAC TTGG (SEQ ID NO: 12) | qPCR | 58 |
| NKX2-5 (NM_001166175.1, NM_001166176.1, NM_004387.3) | ACAACTTCGTGAACT TCGGCG (SEQ ID NO: 13) | GTGGACACTCCCGAG TTGCTCT (SEQ ID NO: 14) | qPCR | 82 |
| TBX5 (NM_000192.3, NM_080717.2, NM_181486.1, NM_080718.1) | TCATAACCAAGGCTG GAAGG (SEQ ID NO: 15) | GCCCGTCACAGACCA TTTAT (SEQ ID NO: 16) | qPCR | 152 |
| ISL1 (NM_002202.2) | CGCCTTGCAGAGTGA CATAG (SEQ ID NO: 17) | GGACTGGCTACCATG CTGTT (SEQ ID NO: 18) | qPCR | 147 |
| MYH6 (α-MHC) (NM_002471) | CTCCTCCTACGCAAC TGCCG (SEQ ID NO: 19) | CGACACCGTCTGGAA GGATGA (SEQ ID NO: 20) | qPCR | 85 |
| MYH7 (β-MHC) (NM_000257) | GACCAGATGAATGAG CACCG (SEQ ID NO: 21) | GGTGAGGTCGTTGAC AGAACG (SEQ ID NO: 22) | qPCR | 63 |
| MLC2v (NM_000432.3) | GGCGCCAACTCCAAC GTGTT (SEQ ID NO: 23) | ACGTTCACTCGCCCA AGGGC (SEQ ID NO: 24) | qPCR | 149 |
| ACTA1 (Skeletal actin) (NM_001100.3) | ACCCAGATCATGTTT GAGACC (SEQ ID NO: 25) | TCATAAATGGGCACG TTGTG (SEQ ID NO: 26) | qPCR | 143 |
| NPPA (ANP) (NM_006172.3) | TCTGCCCTCCTAAAA AGCAA (SEQ ID NO: 27) | TGTCCTCCCTGGCTG TTATC (SEQ ID NO: 28) | qPCR | 156 |
| CASQ2 (NM_001232.3) | TCTTGCAGGGCAGAA GAGGGG (SEQ ID NO: 29) | GGACCTGGGCCACAA GCTCAA (SEQ ID NO: 30) | qPCR | 205 |
| NEUROD1 (NM_002500.3) | AGCCACGGATCAATC TTCTC (SEQ ID NO: 31) | GCGTGCCTCTAATCA TGAAA (SEQ ID NO: 32) | qPCR | 143 |
| CDH1 (ECAD) (NM_004360.3) | GAACGCATTGCCACA TACAC (SEQ ID NO: 33) | ATTCGGGCTTGTTGT CATTC (SEQ ID NO: 34) | qPCR | 118 |
| CDH2 (NCAD) (NM_001792.3) | CCTGGAACGCAGTGT ACAGA (SEQ ID NO: 35) | TGGTTTGACCACGGT GACTA (SEQ ID NO: 36) | qPCR | 104 |
| SNAIL1 (NM_005985.3) | AGCGAGCTGCAGGAC TCTAA (SEQ ID NO: 37) | GGACAGAGTCCCAGA TGAGC (SEQ ID NO: 38) | qPCR | 136 |

TABLE 1-continued

| Gene (Acc #) | F | R | Purpose | Size (bp) |
|---|---|---|---|---|
| MESP1[1] (NM_018670.3) | AGCCCAAGTGACAAGGGACAACT (SEQ ID NO: 39) | AAGGAACCACTTCGAAGGTGCTGA (SEQ ID NO: 40) | qPCR | 82 |
| SOX17[1] (NM_022454.3) | AGGAAATCCTCAGACTCCTGGGTT (SEQ ID NO: 41) | CCCAAACTGTTCAAGTGGCAGACA (SEQ ID NO: 42) | qPCR | 111 |
| ATP2A2 (SERCA2) (NM_001681.3 NM_170665.3) | ACCTCATCTCGTCCAACGTC (SEQ ID NO: 43) | TGTCACCAGATTGACCCAGA (SEQ ID NO: 44) | qPCR | 110 |
| PLN (NM_002667.3) | ACAGCTGCCAAGGCTACCTA (SEQ ID NO: 45) | TCCATGATACCAGCAGGACA (SEQ ID NO: 46) | qPCR | 114 |
| RYR2 (NM_001035.2) | TGCAAGACTCACCGAAGATG (SEQ ID NO: 47) | CCACCCAGACATTAGCAGGT (SEQ ID NO: 48) | qPCR | 125 |
| COL1A1 (NM_000088.3) | GTGCTAAAGGTGCCAATGGT (SEQ ID NO: 49) | ACCAGGTTCACCGCTGTTAC (SEQ ID NO: 50) | qPCR | 128 |
| COL3A1 (NM_000090.3) | CCAGGAGCTAACGGTCTCAG (SEQ ID NO: 51) | CAGGGTTTCCATCTCTTCCA (SEQ ID NO: 52) | qPCR | 103 |
| COL5A1 (NM_000093.3) | GACACCTCCAACTCCTCCAA (SEQ ID NO: 53) | AGTGAACTCCCCCTCCAAGT (SEQ ID NO: 54) | qPCR | 72 |
| COL4A1 (NM_001845.4) | GTTGGTCTACCGGGACTCAA (SEQ ID NO: 55) | GTTCACCTCTGATCCCCTGA (SEQ ID NO: 56) | qPCR | 145 |
| LAMC1 (NM_002293.3) | GTGAGAGGTGCCGAGAGAAC (SEQ ID NO: 57) | GTGCTTAGAGAGCCCACAGG (SEQ ID NO: 58) | qPCR | 88 |
| TGFB2 (NM_001135599.2, NM_0032.38.3) | CGAACCCAAAGGGTACAATG (SEQ ID NO: 59) | TAAGCTCAGGACCCTGCTGT (SEQ ID NO: 60) | qPCR | 91 |
| TTN Ex49-50 (ALL TTN)[2] (NM_001267550.1 NM_001256850.1 NM_133437.3 NM_133432.3 NM_003319.4) | GTAAAAGAGCTGCCCCAGTGA (SEQ ID NO: 61) | GCTAGGTGGCCCAGTGCTACT (SEQ ID NO: 62) | qPCR | 68 |
| TTN Ex107-108 (N2BA)[2] (NM_001267550.1 NM_001256850.1 NM_133378.4) | CAGCAGAACTCAGAATCGA (SEQ ID NO: 63) | ATCAAAGGACACTTCACACTC (SEQ ID NO: 64) | qPCR | 110 |
| TTN Ex50-219 (N2B)[2] (NM_133437.3 NM_133432.3 NM_003319.4) | CCAATGAGTATGGCAGTGTCA (SEQ ID NO: 65) | TACGTTCCGGAAGTAATTTGC (SEQ ID NO: 66) | qPCR | 93 |
| endoOCT4[3] (NM_002701, NM_203289, NM_001173531) | CCTCACTTCACTGCACTGTA (SEQ ID NO: 67) | CAGGTTTTCTTTCCCTAGCT (SEQ ID NO: 68) | RT-PCR | 164 |
| endoSOX2[3] (NM_003106.3) | CCCAGCAGACTTCACATGT (SEQ ID NO: 69) | CCTCCCATTTCCCTCGTTTT (SEQ ID NO: 70) | RT-PCR | 151 |
| endoKLF4[3] (NM_004235.4) | GATGAACTGACCAGGCACTA (SEQ ID NO: 71) | GTGGGTCATATCCACTGTCT (SEQ ID NO: 72) | RT-PCR | 145 |

TABLE 1-continued

| Gene (Acc #) | F | R | Purpose | Size (bp) |
|---|---|---|---|---|
| endoMYC[3] (NM_002467.4) | TGCCTCAAATTGGAC TTTGG (SEQ ID NO: 73) | GATTGAAATTCTGTG TAACTGC (SEQ ID NO: 74) | RT-PCR | 192 |
| SeV | GGATCACTAGGTGAT ATCGAGC (SEQ ID NO: 75) | ACCAGACAAGAGTTT AAGAGATATGTATC (SEQ ID NO: 76) | RT-PCR | 181 |
| BS OCT4-2[4] | TTAGGAAAATGGGTA GTAGGGATTT (SEQ ID NO: 77) | TACCCAAAAAACAAA TAAATTATAAAACCT (SEQ ID NO: 78) | BS | 296 |
| BS OCT4-4[4] | GGATGTTATTAAGAT GAAGATAGTTGG (SEQ ID NO: 79) | CCTAAACTCCCCTTC AAAATCTATT (SEQ ID NO: 80) | BS | 406 |

1. Kattman, et al. *Cell Stem Cell* 8, 228-240 (2011).
2. Neagoe, et al. *Circulation* 106, 1333-1341 (2002).
3. Park, et al. *Nature* 451, 141-146 (2008).
4. Freberg, et al. *Mol Biol Cell* 18, 1543-1553 (2007).

Immunostaining

Digested cardiac differentiation cells were plated on 0.1% gelatin coated glass coverslips for 24 h in 20% FBS (Gibco) in RPMI 1640 supplemented with 1 mmol/L sodium pyruvate, 100 IU/ml Penicillin and 100 µg/ml Streptomycin. The cells were then fixed in Histofix (Roti) for 10 min at room temperature. The cells were then blocked for 30 min in 5% FBS, 1% bovine serum albumin (Sigma) and 0.5% Triton X-100 (Sigma) in PBS (blocking buffer). The cells were then stained with primary antibodies in blocking buffer for 90 min followed by secondary antibodies in blocking buffer and Hoechst for 60 min at room temperature (Table 2). Stained cells were imaged using a Zeiss 710 confocal microscope.

TABLE 2

Antibodies and stains

| Antibody/Stain | Supplier | Cat No. | Marker | Dilution |
|---|---|---|---|---|
| IgG₁ | RnD Systems | MAB002 | Control | 1:100 FC<br>1:100 IF |
| TRA-1-60-FITC (mouse) | BD Pharmingen | 560173 | Pluripotency | 1:100 FC<br>1:100 IF |
| OCT3/4 (rabbit) | Santa Cruz Bio-technology | sc-9081 | Pluripotency | 1:200 FC<br>1:200 IF |
| NANOG (goat) | RnD Systems | AF1997 | Pluripotency | 1:20 IF |
| α-smooth muscle actin (mouse) | Sigma | A2547 | Stromal cell (used predominately in this study) | 1:4000 FC<br>1:400 IF |
| α-smooth muscle actin (rabbit) | Abcam | ab32575 | Stromal cell (used only with α-actinin co-staining) | 1:50 FC |
| Collagen I (rabbit) | Abcam | ab34710 | Stromal cell | 1:2000 FC<br>1:500 IF |
| NKX2-5 (rabbit) | Santa Cruz Bio-technology | H-114 | Cardiomyocyte/cardiac progenitor | 1:200 IF |
| α-actinin (mouse) | Sigma | A7811 | Cardiomyocyte | 1:4000 FC<br>1:1000 IF |
| Cardiac Troponin I (mouse) | Millipore | MAB1691 | Cardiomyocyte | 1:200 IF |
| SIRPA (mouse) | Biolegend | 323802 | Cardiomyocyte | 1:100 FC |
| PDGFRα (mouse) | RnD Systems | MAB1264 | Mesodermal progenitor | 1:25 FC |
| CD90 (mouse) | RnD Systems | MAB2067 | Stromal cell | 1:125 IF<br>1:500 FC |
| Donkey anti-goat Alexafluor 546 | Invitrogen | A-11056 | NA | 1:400 IF |
| Goat anti-mouse Alexafluor 488 | Invitrogen | A-11001 | NA | 1:1000 FC<br>1:400 IF |
| Goat anti-rabbit Alexafluor 546 | Invitrogen | A-11010 | NA | 1:1000 FC<br>1:400 IF |
| Phalloidin Alexafluor 546 | Invitrogen | A22283 | NA | 1:50 IF |
| Hoechst33342 | Invitrogen | H3570 | NA | 1:1000 FC<br>1:1000 IF |

(FC—Flow cytometry, IF—Immunofluorescence)

Whole-Mount Immuno-Staining BHMs were fixed in Histofix for 2-4 h at 4° C. The BHMs were then stained with primary antibodies for 2-3 days followed by secondary antibodies and Phalloidin 546/Hoechst for 2-3 days at 4° C. (Table 2). Stained BHMs were imaged using a Zeiss 710 confocal microscope.

Flow Cytometry

Cells were stained either live or fixed using Histofix for 10 min at room temperature or ethanol. The cells were stained in 5% FBS in PBS (membrane blocking buffer) for cell surface markers (excluding TRA-1-60) and blocking buffer for internal markers. The cells were then stained with primary antibodies in blocking buffer for 45 min followed by secondary antibodies in blocking buffer and Hoechst for 30 min at 4° C. (Table 2). A BD LSRII was used for flow cytometry analysis (BD Biosystems). Live cells populations were gated based on forward-side scatter profiles; fixed cells populations were gated based on Hoechst staining. BD FACSDiva Software (BD Bioscience) or Cyflologic v1.2.1 (Cyflo Ltd) were used for analysis.

Contraction Measurements

Contraction experiments were performed in organ baths at 37° C. and continuous bubbling with 5% $CO_2$/95% $O_2$ to maintain a physiological pH in Tyrode's solution containing (all in mM): 120 NaCl, 1 $MgCl_2$, 0.2 $CaCl_2$, 5.4 KCl, 22.6 $NaHCO_3$, 4.2 $NaH_2PO_4$, 5.6 glucose and 0.56 ascorbate. Calcium was adjusted using a 0.2 M calcium chloride solution. All BHM were first analysed at 3 Hz with 5 ms square pulses of 200 mA in order to pace at approximately the embryonic heart rate. BHM were mechanically stretched at intervals of 125 μm until Lmax, i.e. the tissue length were maximum twitch tension/force of contraction was recorded in the presence of maximally inotropically active calcium concentrations (2 mmol/L; Frank-Starling mechanism). Subsequently, BHM were subjected to different calcium concentrations (0.2, 0.4, 0.8, 1.2, 1.6, 2.0, 2.4 mM) and the twitch force recorded. For isoprenaline experiments the calcium concentration was adjusted to 0.6 mM and subsequently the isoprenaline concentration was adjusted to 1 μM.

Oxygen Diffusion Profile

The oxygen diffusion profile was generated using numerical analysis of a pseudosteady-state approximation of cylinder diffusion with oxygen consumption dependence on concentration (Eq. 1). Parameters from the literature (Brown et al. Biotechnol Bioeng 97, 962-075 (2007)) and as determined in previous experiments were used (Table 3). Numerical analysis and plotting was performed using MATLAB V12 (Mathworks) using the solver bvp4c and the Singular Term option.

$$0 = \frac{-D_{O2}}{r}\left[r\frac{dC_{O2}}{dr}\right] + V_{max}\rho_{cardiomyocyte}e^{\left(\frac{-\alpha}{C_{O2}}\right)} \quad \text{Eq. 1}$$

$C_{O2}$—oxygen concentration as a function of radial position, r—radial position in cylinder, $D_{O2}$—oxygen diffusion constant, $V_{max}$—maximal oxygen generation rate by cardiomyocytes, $\rho_{cardiomyocyte}$—density of cardiomyocytes, α—constant for oxygen generation rate dependence on oxygen concentration.

TABLE 3

Oxygen diffusion model parameters

| Model Parameter | Value |
|---|---|
| $D_{O2}$ | $2 \times 10^5$ cm²/s |
| $P_{cardiomyocyte}$ | $\rho_{cardiomyocyte} = \frac{\text{CellNumber} \cdot \text{CardiomyocytePurity}}{\text{BHMVolume}}$ |
| $V_{max}$ | $-5.44 \times 10^{-8}$ nmol/cell/s |

TABLE 3-continued

Oxygen diffusion model parameters

| Model Parameter | Value |
|---|---|
| α | Calculated to fit oxygen consumption-concentration relationship from [5]; 1.14 μM |
| Bounding Conditions | |
| At r = 0; $\frac{dC_{O2}}{dr} = 0$ | |
| At r = R; $C_{O2} = C^*$ | R = 0.5 mm; $C^* = 61$ μM |

5. Brown, et al. Biotechnol Bioeng 97, 962-975 (2007).

Statistical Analysis

All data is presented as mean±s.e.m. Appropriate statistical analyses were used for each data set as indicated in the Figure legends using Graph Pad Prism or Microsoft Excel.

Custom-Made Supplement to Replace B27®

TABLE 4

Custom-made supplement (CMS) to replace B27.

| Substance | Final concentration | 25x | Supplier |
|---|---|---|---|
| Albumin | 5 mg/ml | 125 mg/ml | Sigma, A9511 |
| Transferrin | 10 μg/ml | 250 μg/ml | Sigma, T0665 |
| EthanolamineHCl | 2 μg/ml | 50 μg/ml | Sigma, E6133 |
| Sodium selenite | 0.032 μg/ml | 0.8 μg/ml | Sigma, S5361 |
| L-CarnitineHCl | 4 μg/ml | 100 μg/ml | Sigma, C0283 |
| Hydrocortisone | 1 μg/ml | 25 μg/ml | Sigma, H2270 |
| Fatty acid supplement | 0.5 μl/ml | 12.5 μl/ml | Sigma, F7050 |
| Triiodo-L-thyronine | 0.004 μg/ml | 0.1 μg/ml | Sigma, T 6397 |

Prepare 25x in cell culture-qualified water.

LIST OF REFERENCES

Kehat, I. et al. Human embryonic stem cells can differentiate into myocytes with structural and functional properties of cardiomyocytes. *J Clin Invest* 108, 407-414 (2001).

Takahashi, K. et al. Induction of pluripotent stem cells from adult human fibroblasts by defined factors. *Cell* 131, 861-872 (2007).

Zhang, J. et al. Functional cardiomyocytes derived from human induced pluripotent stem cells. *Circ Res* 104, e30-41 (2009).

Thomson, J. A. et al. Embryonic stem cell lines derived from human blastocysts. *Science* 282, 1145-1147 (1998).

Lian, X., Zhang, J., Zhu, K., Kamp, T. J. & Palecek, S. P. Insulin Inhibits Cardiac Mesoderm, not Mesendoderm, formation during Cardiac Differentiation of Human Pluripotent Stem Cells and Modulation of Canonical Wnt Signaling Can Rescue this Inhibition. *Stem Cells* 31(3), 447-457 (2013).

Schaaf, S. et al. Human engineered heart tissue as a versatile tool in basic research and preclinical toxicology. *PLoS ONE* 6, 20 (2011).

Carvajal-Vergara, X. et al. Patient-specific induced pluripotent stem-cell-derived models of LEOPARD syndrome. *Nature* 465, 808-812 (2010).

Itzhaki, I. et al. Modelling the long QT syndrome with induced pluripotent stem cells. *Nature* 471, 225-229 (2011).

Malan, D., Friedrichs, S., Fleischmann, B. K. & Sasse, P. Cardiomyocytes obtained from induced pluripotent stem cells with long-QT syndrome 3 recapitulate typical disease-specific features In Vitro. *Circ Res* 109(8), 841-847 (2011).

Moretti, A. et al. Patient-specific induced pluripotent stem-cell models for long-QT syndrome. *N Engl J Med* 363, 1397-1409 (2010).

Yazawa, M. et al. Using induced pluripotent stem cells to investigate cardiac phenotypes in Timothy syndrome. *Nature* 471, 230-234 (2010).

Bird, S. D. et al. The human adult cardiomyocyte phenotype. *Cardiovasc Res* 58, 423-434 (2003).

Eschenhagen, T. et al. Three-dimensional reconstitution of embryonic cardiomyocytes in a collagen matrix: a new heart muscle model system. *FASEB J* 11, 683-694 (1997).

Zimmermann, W. H. et al. Tissue engineering of a differentiated cardiac muscle construct. *Circ Res* 90, 223-230 (2002).

Tulloch, N. L. et al. Growth of engineered human myocardium with mechanical loading and vascular coculture. *Circ Res* 109, 47-59 (2011).

Tiburcy, M. et al. Terminal differentiation, advanced organotypic maturation, and modeling of hypertrophic growth in engineered heart tissue. *Circ Res* 109, 1105-1114 (2011).

Eschenhagen, T., Eder, A., Vollert, I. & Hansen, A. Physiological aspects of cardiac tissue engineering. *Am J Physiol Heart Circ Physiol* 303, 11 (2012).

Hudson, J. E., Brooke, G., Blair, C., Wolvetang, E. & Cooper-White, J. J. Development of myocardial constructs using modulus-matched acrylated polypropylene glycol triol substrate and different nonmyocyte cell populations. *Tissue Eng Part A* 17, 2279-2289 (2011)

Hudson, J., Titmarsh, D., Hidalgo, A., Wolvetang, E. & Cooper-White, J. Primitive cardiac cells from human embryonic stem cells. *Stem Cells Dev* 21, 1513-1523 (2012).

Cao, N. et al. Ascorbic acid enhances the cardiac differentiation of induced pluripotent stem cells through promoting the proliferation of cardiac progenitor cells. *Cell Res* 22, 219-236 (2012).

Kruithof, B. P., Duim, S. N., Moerkamp, A. T. & Goumans, M. J. TGFbeta and BMP signaling in cardiac cushion formation: lessons from mice and chicken. *Differentiation* 84, 89-102 (2012).

Brown, D. A. et al. Analysis of oxygen transport in a diffusion-limited model of engineered heart tissue. *Biotechnol Bioeng* 97, 962-975 (2007).

Ellerstrom, C., Strehl, R., Noaksson, K., Hyllner, J. & Semb, H. Facilitated expansion of human embryonic stem cells by single-cell enzymatic dissociation. *Stem Cells* 25, 1690-1696 (2007).

Chan, E. M. et al. Live cell imaging distinguishes bona fide human iPS cells from partially reprogrammed cells. *Nat Biotechnol* 27, 1033-1037 (2009).

Freberg, C. T., Dahl, J. A., Timoskainen, S. & Collas, P. Epigenetic reprogramming of OCT4 and NANOG regulatory regions by embryonal carcinoma cell extract. *Mol Biol Cell* 18, 1543-1553 (2007).

Campos, P. B., Sartore, R. C., Abdalla, S. N. & Rehen, S. K. Chromosomal spread preparation of human embryonic stem cells for karyotyping. *J Vis Exp* 4 (2009).

Kattman, S. J. et al. Stage-specific optimization of activin/nodal and BMP signaling promotes cardiac differentiation of mouse and human pluripotent stem cell lines. *Cell Stem Cell* 8, 228-240 (2011).

Neagoe, C. et al. Titin isoform switch in ischemic human heart disease. *Circulation* 106, 1333-1341 (2002).

Park, I. H. et al. Reprogramming of human somatic cells to pluripotency with defined factors. *Nature* 451, 141-146 (2008).

Thomson, J. A., et al. Embryonic stem cell lines derived from human blastocysts. *Science* 282, 1145-1147 (1998).

Takahashi, K. & Yamanaka, S. Induction of pluripotent stem cells from mouse embryonic and adult fibroblast cultures by defined factors. *Cell* 126, 663-676 (2006).

Didié et al. Parthenogenetic stem cells for tissue-engineered heart repair. *J Clin Invest.* 123, 1285-1298 (2013).

Irion, S et al. Identification and targeting of the ROSA26 locus in human embryonic stem cells. *Nat Biotechnol* 25, 1477-1482 (2007)

Naito, H. et al. Optimizing engineered heart tissue for therapeutic applications as surrogate heart muscle. *Circulation* 114, 172-78 (2006).

Zimmermann W. H. et al. Three-dimensional engineered heart tissue from neonatal rat cardiac myocytes. *Biotechnol Bioeng* 68, 106-114 (2000).

Zimmermann W. H. et al. Engineered heart tissue grafts improve systolic and diastolic function in infarcted rat hearts. *Nat Med* 12, 452-458 (2006).

The invention claimed is:

1. A method for producing bioengineered heart muscle from pluripotent stem cells, comprising the steps of
    (i) cultivating pluripotent stem cells in a basal medium comprising an effective amount of (a) BMP4, Activin A, FGF2, a GSK3-inhibitor, and (b) a serum-free supplement resulting in a final concentration of 0.5-50 mg/ml albumin, 1-100 µg/ml transferrin, 0.1-10 µg/ml ethanol amine, 0.003-0.3 µg/ml sodium selenite, 0.4-40 µg/ml L-Carnitine HCl, 0.1-10 µg/ml Hydrocortisone, 0.05-5 µl/ml Fatty acid supplement, and 0.0001-0.1 µg/ml triodo-L-thyronine (T3), thereby inducing mesoderm differentiation of said pluripotent stem cells;
    (ii) cultivating the cells obtained in step (i) in a basal medium comprising an effective amount of an inhibitor of the Wnt-signaling pathway and a serum-free supplement as in (i), thereby inducing cardiac differentiation of the cells; and
    (iii) cultivating the cells obtained in step (ii) in a basal medium comprising an effective amount of a serum-free supplement as in (i), under mechanical stimulation, thereby promoting cardiac maturation, wherein prior to step (i) said pluripotent stem cells are seeded in the presence of callogen in a mould.

2. The method of claim 1, wherein the pluripotent stem cells are selected from embryonic stem cells, induced pluripotent stem cells, and parthenogenetic stem cells.

3. The method of claim 1, wherein the pluripotent stem cells are pluripotent stem cells of primate origin.

4. The method of claim 3, wherein the pluripotent stem cells are human pluripotent stem cells.

5. The method of claim 1, wherein the basal medium in step (i) comprises
    1-20 ng/ml BMP4; and
    0.1-10 ng/ml FGF2; and
    1-20 ng/ml Activin A.

6. The method of claim 5, wherein the basal medium in step (i) comprises about 5 ng/ml BMP4; or about 5 ng/ml FGF2; or about 9 ng/ml Activin A; or a combination thereof.

7. The method of claim 1, wherein the GSK3-inhibitor in the basal medium of step (i) is selected from the group consisting of CHIR99021, CHIR98014, SB216763, TWS119, Tideglusib, SB415286, and LY2090314.

8. The method of claim 7, wherein the basal medium in step (i) comprises 0.1-10 µM CHIR99021.

9. The method of claim 1, wherein the inhibitor of the Wnt-signaling pathway in the basal medium of step (ii) is selected from the group consisting of IWP4, IWP2, IWR-1, IWP1, IWP3, IWR-2, IWR-3, IWR-4, IWR-5, XAV939, DKK1, quercetin, ICG-001, pyrvinium, CCT031374, iCRT-3,5,14, CPG049090, NC043.

10. The method of claim 9, wherein the basal medium of step (ii) comprises 0.1-10 µM IWP4.

11. The method of claim 1, wherein the basal medium of step
    a) further comprises 0.1-10 ng/ml TGFβ1; or
    b) does not comprise an effective amount of FGF2; or
    c) comprises 0.5-3 mM $Ca^{2+}$; or
    d) comprises a combination of any one of a), b), and c).

12. The method of claim 11, wherein the basal medium of step (iii) comprises about 1 ng/ml TGFβ1; or about 1.2 mM $Ca^{2+}$; or a combination thereof.

13. The method of claim 1, wherein the mechanical stimulation in step (iii) is dynamic mechanical stimulation or static stretch.

14. The method of claim 13, wherein the mechanical stimulation in step (iii) is dynamic mechanical stimulation.

15. The method of claim 1, wherein the basal medium of any one of step (i), (ii) or (iii) comprises 10-1000 µM of ascorbic acid or a salt or a derivative thereof.

16. The method of claim 1, wherein the basal medium used in any one of step (i), (ii) or (iii) is DMEM/F12, Iscove's medium, αMEM, DMEM, and RPMI.

17. The method of claim 16, wherein the basal medium used in any one of step (i), (ii) or (iii) is RPMI supplemented with pyruvate.

18. The method of claim 1, comprising prior to step (i) a seeding step, wherein said pluripotent stem cells are seeded in a ratio of $(2.5\text{-}6\times10^6$ cells/1 mg collagen)/1 ml medium in a suitable mould.

19. The method of claim 18, wherein the seeding step is carried out 18-30 h prior to step (i).

20. The method of claim 18, wherein the medium used in the seeding step further comprises a ROCK-inhibitor.

21. The method of claim 20, wherein the ROCK-inhibitor is selected from Y27632, H-1152P, Thiazovivin, Fasudil, Hydroxyfasudil, GSK429286A, and RKI-1447.

22. The method of claim 20, wherein the medium used in the seeding step comprises 1-50 µM Y27632.

23. The method of claim 1, wherein said pluripotent stem cells are not produced using a process which involves modifying the germ line genetic identity of human beings or which involves use of a human embryo for industrial or commercial purposes.

* * * * *